(12) United States Patent
Ott et al.

(10) Patent No.: US 9,820,794 B2
(45) Date of Patent: Nov. 21, 2017

(54) DEVICES FOR KILLING TUMOR CELLS AND RELATED SYSTEMS AND METHODS

(75) Inventors: Mark John Ott, Salt Lake City, UT (US); Troy J. Orr, Draper, UT (US)

(73) Assignee: Intermountain Invention Management, LLC, Salt Lake City, UT (US)

( * ) Notice: Subject to any disclaimer, the term of this patent is extended or adjusted under 35 U.S.C. 154(b) by 949 days.

(21) Appl. No.: 13/988,243

(22) PCT Filed: Nov. 21, 2011

(86) PCT No.: PCT/US2011/061696
§ 371 (c)(1),
(2), (4) Date: Jul. 30, 2013

(87) PCT Pub. No.: WO2012/068580
PCT Pub. Date: May 24, 2012

(65) Prior Publication Data
US 2013/0324986 A1     Dec. 5, 2013

Related U.S. Application Data

(60) Provisional application No. 61/415,478, filed on Nov. 19, 2010.

(51) Int. Cl.
*A61B 18/08* (2006.01)
*A61B 18/02* (2006.01)
(Continued)

(52) U.S. Cl.
CPC .............. *A61B 18/02* (2013.01); *A61B 18/08* (2013.01); *A61B 18/14* (2013.01);
(Continued)

(58) Field of Classification Search
CPC ......... A61B 18/02; A61B 18/08; A61B 18/12; A61B 18/14; A61B 18/1466;
(Continued)

(56) References Cited

U.S. PATENT DOCUMENTS

| 3,845,771 A | 11/1974 | Vise |
| 4,337,496 A | 6/1982 | Laird |

(Continued)

FOREIGN PATENT DOCUMENTS

| DE | 20315652 | 1/2004 |
| WO | WO2012068580 | 5/2012 |

OTHER PUBLICATIONS

International Search Report and Written Opinion dated Nov. 21, 2011 for PCT/US2011/061696.

*Primary Examiner* — Michael Peffley
*Assistant Examiner* — Khadijeh Vahdat
(74) *Attorney, Agent, or Firm* — Stoel Rives LLP

(57) ABSTRACT

Various devices, systems, and methods are capable of killing tumor cells by delivering cell-disrupting agents into a tumor in an inward direction from a peripheral border about the tumor. In some examples, a covering that includes one or more emissive elements encompasses at least a portion of a tumor such that the emissive element is directed inwardly toward the tumor so as to be able to introduce a cell-disrupting agent into the tumor. In further examples, the covering is incorporated into a glove.

22 Claims, 24 Drawing Sheets

(51) Int. Cl.
*A61B 18/18* (2006.01)
*A61B 18/14* (2006.01)
*A61B 18/12* (2006.01)
*A61N 7/02* (2006.01)
*A61B 90/30* (2016.01)
*A61B 90/00* (2016.01)
*A61B 42/00* (2016.01)

(52) U.S. Cl.
CPC .......... *A61B 18/1815* (2013.01); *A61B 18/12* (2013.01); *A61B 42/00* (2016.02); *A61B 90/30* (2016.02); *A61B 90/361* (2016.02); *A61N 7/02* (2013.01)

(58) Field of Classification Search
CPC ............ A61B 18/1442; A61B 18/1445; A61B 18/1448; A61B 18/18; A61B 18/1815; A61B 19/04; A61B 19/5202; A61B 19/5212; A61N 7/02
USPC ............................... 606/1, 13, 20–27, 33–50
See application file for complete search history.

(56) References Cited

U.S. PATENT DOCUMENTS

| | | |
|---|---|---|
| 4,510,939 A | 4/1985 | Brenman et al. |
| 4,957,481 A | 9/1990 | Gatenby |
| 5,120,304 A | 6/1992 | Sasaki |
| 5,242,440 A | 9/1993 | Shippert |
| 5,359,996 A | 11/1994 | Hood |
| 5,507,743 A | 4/1996 | Edwards et al. |
| 5,562,609 A | 10/1996 | Brumbach |
| 5,947,922 A | 9/1999 | MacLeod |
| 7,270,658 B2 | 9/2007 | Woloszko et al. |
| 2002/0058934 A1 | 5/2002 | Wang et al. |
| 2003/0060822 A1 | 3/2003 | Schaer et al. |
| 2004/0260281 A1 | 12/2004 | Baxter, III et al. |
| 2006/0247614 A1 | 11/2006 | Sampson et al. |
| 2007/0093807 A1 | 4/2007 | Baxter, III et al. |
| 2007/0225702 A1 | 9/2007 | Kaouk |
| 2008/0071262 A1* | 3/2008 | Azure ................ A61B 18/1477 606/34 |
| 2008/0208294 A1 | 8/2008 | Pierce |
| 2009/0228001 A1* | 9/2009 | Pacey ................ A61B 18/1477 606/33 |

* cited by examiner

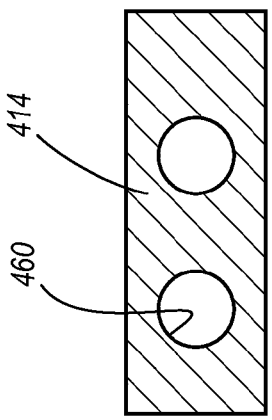
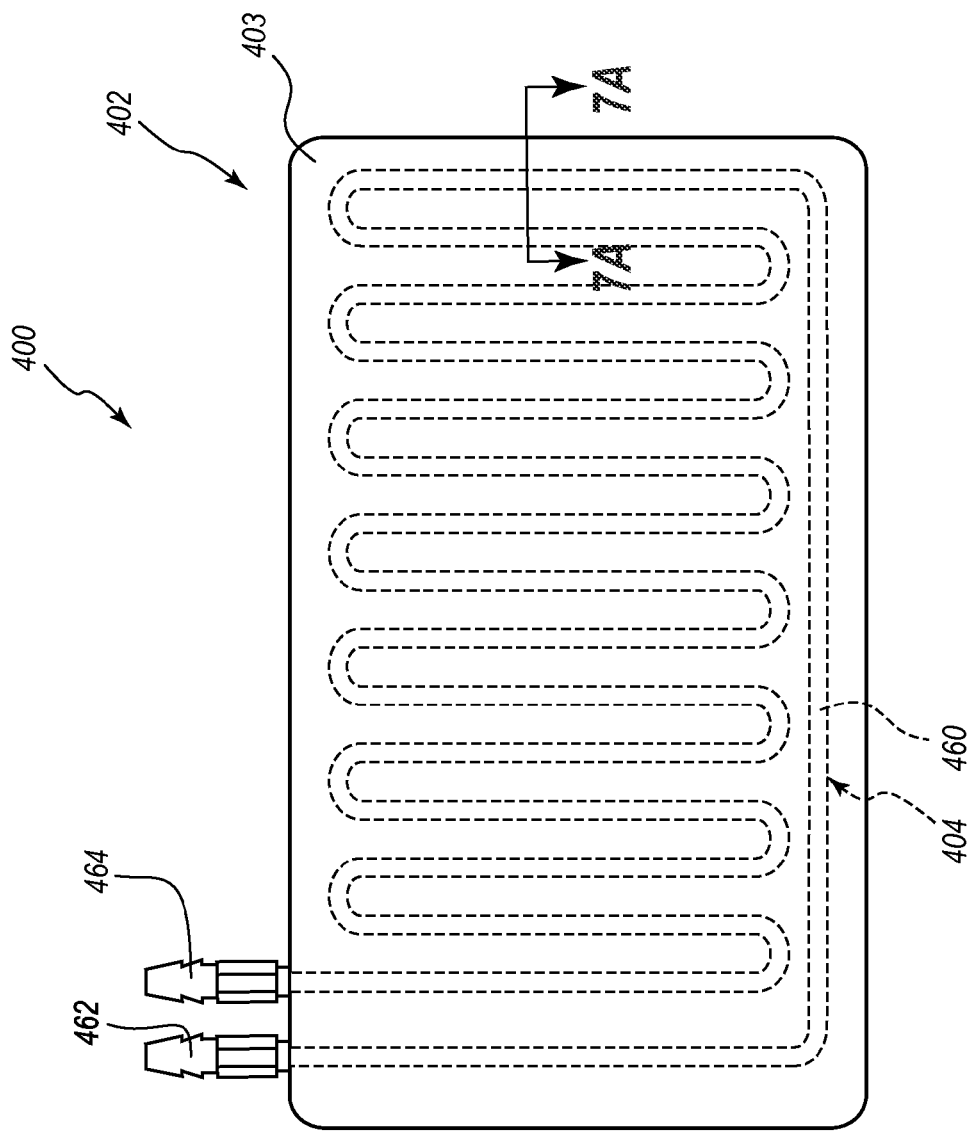

DEVICES FOR KILLING TUMOR CELLS AND RELATED SYSTEMS AND METHODS

TECHNICAL FIELD

The present disclosure relates to devices, systems, and methods for killing tumor cells, such as those of tumors that are not amenable to resection.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 7 is a top plan view of another embodiment of a cover that is compatible with systems for killing tumor cells;

FIG. 7A is partial cross-sectional view of the cover of FIG. 7 taken along the line 7A-7A in FIG. 7;

DETAILED DESCRIPTION

It is not uncommon for a surgeon to explore a patient for a solid organ tumor and find that the tumor is unresectable due to local involvement of critical blood vessels, nerves, and/or other structures. The tumor may be separable from surrounding tissue, and may even be graspable within the hand of the surgeon, yet the presence of important structures may nevertheless prevent removal of the tumor.

Disclosed herein are various embodiments of systems that can be used generally in the treatment of tumors and/or any other tissue that may desirably be killed. Certain systems can be particularly useful for the treatment of tumors that are not amenable to resection, or that are fully unresectable, such as those just described. In some instances, a tumor can be partially or fully isolated from surrounding healthy tissue such that an outer border is defined about the tumor. One or more transfer elements may be placed about the tumor, from which one or more cell-disrupting agents can be introduced into the tumor. Accordingly, the cell-disrupting agents can move from the outer border about the tumor toward an interior of the tumor.

In some embodiments, the one or more transfer elements are included in a glove, such that the tumor may be held in a hand that is within the glove during delivery of the one or more cell-disrupting agents. The glove can allow for tactile feedback to its user, which can be particularly advantageous in some instances, such as those in which direct contact between the transfer elements and the outer border of the tumor is desirable (e.g., where heat transfer takes place between the transfer elements and the tumor).

In still other or further embodiments, the glove may include surgical features that can assist in the creation of a border about the tumor. For example, in some embodiments, a glove can include electrosurgical features, which can allow for cutting, ablation, coagulation, and/or welding tissue.

Various advantages of the systems that are described herein relative to the prior art will be evident from the disclosure. For example, certain embodiments may be more effective than known treatments for tumors. Such known treatments include probes or other devices that are inserted into the tumors in order to perform cryotherapy, heat ablation (e.g., radiofrequency ablation or microwave therapy), or chemical injury (e.g., alcohol ablation). Each of these known therapies works from the inside out, and thus may be effective over only a small volume within the tumor, or stated otherwise, may be ineffective at reaching and killing tumor cells that are at the outer margin of the tumor. Moreover, with such prior art arrangements, it can be difficult to monitor conditions at the outer regions of the tumor to determine whether all tumor cells are likely to have been killed.

Figure 1:
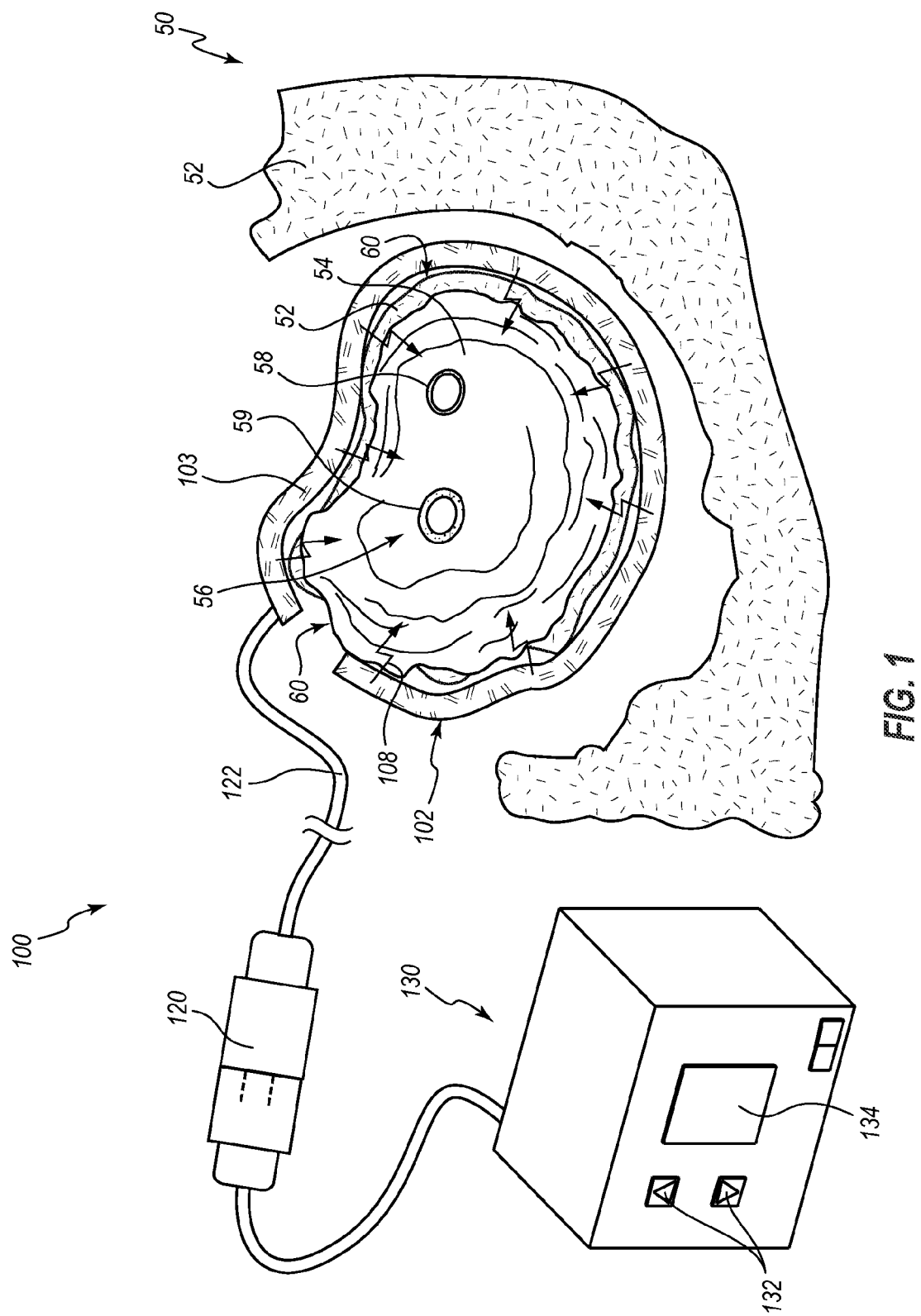
FIG. 1 is a perspective and elevation view of an embodiment of a system for killing tumor cells.
Figure 3:
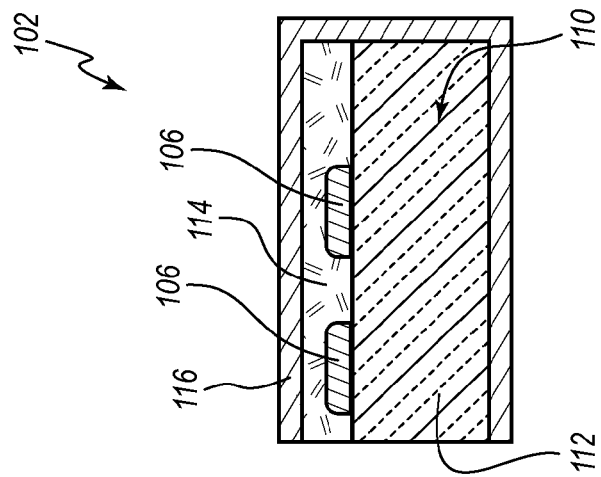
FIG. 3 is a partial cross-sectional view of the cover of FIG. 2 taken along the view line 3-3 in FIG. 2.
Figure 2:
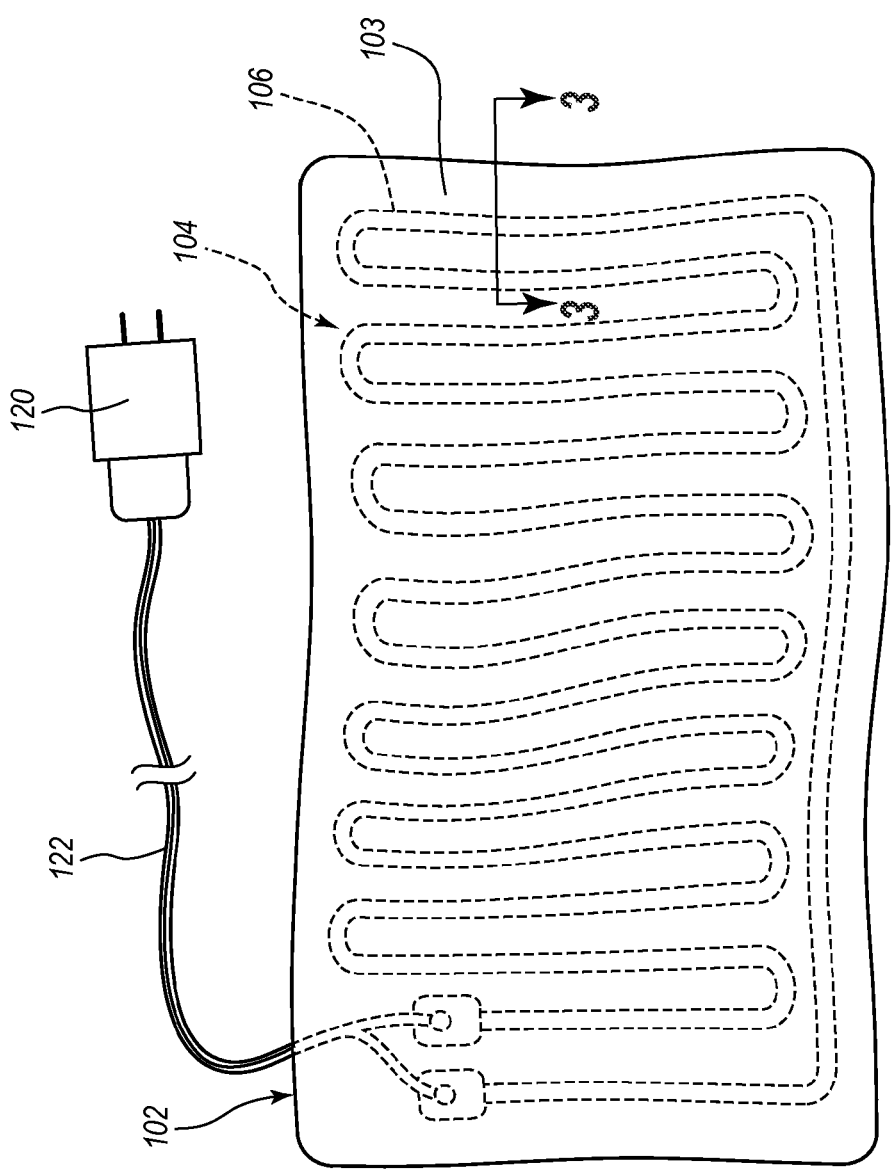
FIG. 2 is a top view an embodiment of a cover that is compatible with the system of FIG. 1.

FIGS. 1-3 illustrate an embodiment of a tumor treatment system 100 that is configured to abate a tumor 54. The term "abate" is used herein in a broad sense that includes killing, disruption, dissolution, and/or any other destructive effect on at least a portion of the tumor, which can result in a reduction or elimination of a size and/or potency of the tumor. Accordingly, a tumor may be abated where cells thereof are removed from the body. A tumor may also be abated where cells thereof are killed, whether or not those cells are ultimately physically removed from the body.

Figure 20:
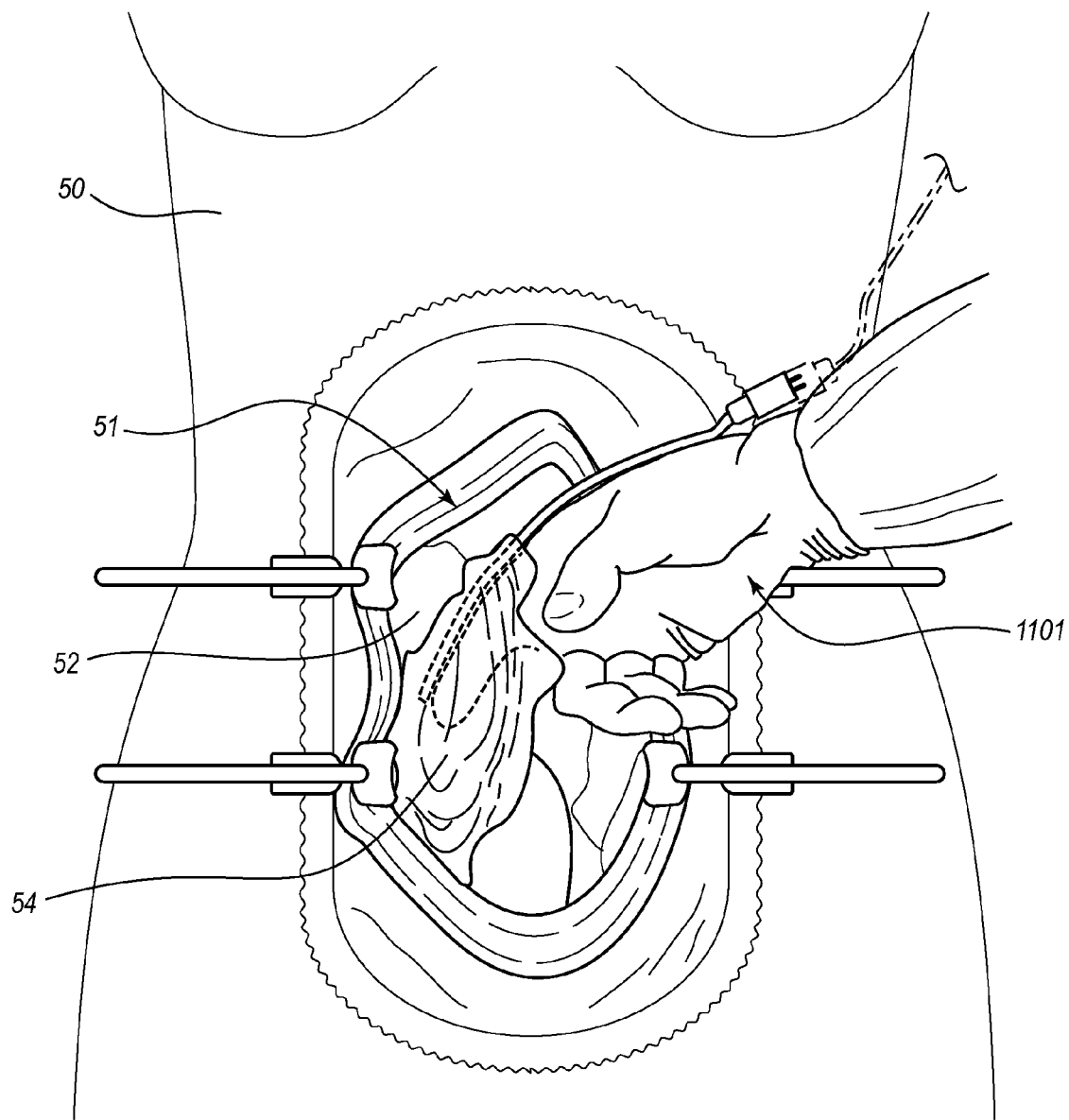
FIG. 20 is a perspective view of the system of FIG. 19 in use.

In FIG. 1, the tumor 54 is shown as having been separated from a section of healthy tissue 52 of a patient 50. Any suitable technique may be used to separate the tumor 54 from the healthy tissue 52. One such surgical method is depicted in FIG. 20, and includes the use of a specialized glove, which is described further below.

With continued reference to FIG. 1, a small amount of healthy tissue 52 may remain with the separated or isolated tumor 54. This can result in the creation of a small margin about at least a portion of the tumor 54, which can help to ensure that all tumor cells have been separated from the patient 50. An outer border 60 thus can extend about at least a portion of the tumor 54. In the illustrated embodiment, the outer border 60 is the outermost peripheral surface of the separated mass, which includes both the tumor 54 and the small margin of healthy tissue 52. Furthermore, in the illustrated embodiment, the outer border 60 is a continuous surface that fully encompasses the tumor 54. In other embodiments, only a portion of the tumor 54 may be separated from the healthy tissue 52, as the outer border 60 may encompass only a portion of the tumor 54 (discussed further below with respect to FIG. 17).

In certain embodiments, the tumor 54 may have sensitive structures 56 that pass through it. For example, one or more major blood vessels 58, 59, nerves (not shown), and/or other structures may pass through the tumor 54 such that resection of the tumor 54 would be detrimental to the health of the patient 50. As a result, in may be desirable to abate the tumor 54 without severing any of the sensitive structures 58, 59. The tumor 54 may be killed without displacing the structures 56 far from their natural orientation within the body of the patient 50. For example, the tumor 54 may be moved only slightly so as to be spaced from the healthy tissue 52 and then subjected to treatments in manners such as described below. As further discussed hereafter, in some instances, the tumor 54 and sensitive structures 56 therein may be returned to the body of the patient 50 after having been subjected to the treatment.

FIGS. 1-3 illustrate an embodiment of a cover 102 that can be used in the system 100 to treat the tumor 54. The cover 102 comprises a blanket, pad, or wrap 103 that is flexible and/or configured so to be movable to conform to a contour defined by the outer border 60 that extends about the tumor 54. For example, the wrap 103 can comprise any suitable elastomeric, pliable, or flexible material that can readily change shape so as to conform to an outer contour of the tumor 54. The cover 102 can comprise one or more transfer elements 104 that are configured to deliver a cell-disrupting agent 108 into the tumor 54. Accordingly, the transfer elements 104 interface with or otherwise interact with the tumor 54 so as to provide the cell-disrupting agent 108 thereto. In the illustrated embodiment, the one or more transfer elements 104 comprise a resistive heating coil 106.

One or more electrical leads 122 can be in electrical communication with the heating coil 106, and may be connected to a controller 130 via a connector 120. The controller 130 may comprise a general-purpose computer, a special-purpose computer, or any other suitable electronic device or control device, and may include buttons 132 or other suitable interfaces for providing instructions to the controller 130. The controller 130 can include a display 134 by which settings of the controller 130 and/or other information regarding operation of the system 100 may be observed or monitored.

As shown in FIG. 3, in some embodiments, the heating coil 106 may be positioned within one or more layers of material that may have different thermally conductive properties. In some embodiments, a first layer 112 may be less thermally conductive than a second layer 114 and/or may be thermally insulating. The cover 102 thus can be oriented such that the first layer 112 faces away from the tumor 54 and the second layer 114 faces toward the tumor 54. The first layer 112 thus may act as a shield or barrier 110 to protect surrounding healthy tissue 52 from high levels of heat, whereas the second layer 114 may readily permit the transfer of heat to the tumor 54. In some embodiments, the cover 102 may comprise a sheath or sleeve 116 that covers or encloses at least a portion of the inner layers 112, 114. The sleeve 116 may, in some embodiments, comprise a bio-compatible material, and may be relatively thermally conductive.

In various embodiments, the cover 102 can comprise any suitable flexible heater that is available from Minco of Minneapolis, Minn., such as any suitable Thermfoil™ heater. For example, in some embodiments, the cover 102 can comprise etched-foil elements that are sandwiched between layers of PTFE.

In the illustrated embodiment, the transfer element 104 is substantially coextensive with the surface area of the cover 102. Accordingly, those portions of the cover 102 that are wrapped about the tumor 54 generally include portions of the transfer element 104. Thus, when the cover 102 is positioned about at least a majority of a perimeter of the tumor 54, the transfer element 104 likewise can be positioned about at least a majority of the perimeter. Accordingly, in some embodiments, the cover 102 may provide cell-disrupting agents to the tumor 54 at opposite sides thereof. Similarly, the barrier 110 may be positioned at opposite sides of the tumor 54 so as to prevent cell-disrupting agents that are introduced at one side of the tumor 54 from progressing through the tumor 54 and into healthy tissue at an opposite side of the tumor 54. In embodiments where the cell-disrupting agent is electromagnetic radiation, as opposed to heat, such shielding on opposing sides of the tumor 54 may have a greater effect.

Illustrative methods for using the cover 102 will now be described. As shown in FIG. 20, in some embodiments, a surgical opening 51 is formed in any suitable manner to provide access to the tumor 54. The tumor 54 is then separated or isolated from the surrounding healthy tissue 52. The separation may proceed using standard techniques or using other techniques, such as those described below with respect to FIG. 20.

With reference to FIG. 1, the tumor 54 is not fully removed from the patient 50, however, due to the vessels 58, 59 or other sensitive structures 56 that pass through the tumor 54. Accordingly, treatment of the tumor 54 can take place in situ. The cover 102 is positioned about at least a majority of the outer border 60 that extends about the tumor 54. In some embodiments, the cover 102 is placed in direct contact with the tumor 54 so as to provide for efficient transfer of heat to the tumor 54. In some embodiments, connection mechanisms (not shown) may be used to secure the cover 102 to the tumor 54 so as to maintain thermal contact between the cover 102 and the tumor 54. In some embodiments, the connection mechanisms can comprise one or more ties, bands, straps, or other connection devices that extend about the cover 102, and/or sutures, staples, or other devices that may be passed through the cover 102 and into the tumor 54. In some embodiments, a high viscosity heat conducting liquid may be applied to the cover 102 before it is positioned about the tumor 54 to aid in heat transfer across the outer border 60. For example, in certain embodiments, Surgilube™ that is available from Fougera, other types of hydrogels that are biologically compatible, or other high viscosity heat conductive liquids may be used.

The appropriate settings may be selected on the controller 130 so as to activate the cover 102 and provide the cell-disrupting agent 108 into the tumor 54. In the illustrated embodiment, the cell-disrupting agent 108 comprises heat from the heating coil 106 that is directed inwardly toward a central region of the tumor 54.

As is known in the art, heat can be used to kill or otherwise disrupt cells when a certain temperature is reached and/or when the temperature is sustained for an effective period. A size of the tumor 54 and/or heating properties of the tumor 54 can be used to determine the amount of energy that will be provided to the tumor 54 via the cover 102. In various embodiments, sufficient heat is supplied to the tumor 54 to raise the temperature of at least a portion of the tumor 54 to no less than about 60, 70, 80, 90, or 100 degrees Celsius. In some embodiments, energy is supplied to the tumor 54 via the cover 102 for a period of no less than about 5, 10, 15, 20, 30, 40, 50, or 60 minutes, or for a period that is within a range of from about 5 to about 30, 40, 50, or 60 minutes, from about 10 to about 30, 40, 50, or 60 minutes, or from about 15 to about 30, 40, 50, or 60 minutes. Tumors of various sizes may be treated via such apparatus and methods. In some instances, the tumors may have a diameter that is in a range of from about 2 centimeters to about 6, 15, 20, or 30 centimeters. In some embodiments, the diameter is no less than about 6, 15, 20, or 30 centimeters.

After application of the cell-disrupting agent 108 into the tumor 54, the tumor 54 can be returned to its original position within the patient 50, and the surgical opening 51 can be closed in any suitable manner. In some embodiments, leaving the treated tumor 54 in the patient may have beneficial effects. For example, where some or all of the cells of the tumor 54 have been killed, the dead cells may be reabsorbed by the body of the patient 50 and may have positive immunological effects.

As can be appreciated from the foregoing, creating a border 60 about at least a portion of the tumor 54 and directing a cell-disrupting agent 108 through the border 60 and inwardly into the tumor 54 can allow for controlled treatment of tumor cells that are at the outer region of the tumor 54. Such an arrangement can also provide a large surface area over which the cell-disrupting agent 108 can be administered, which can result in a relatively shorter treatment period that may proceed at weaker levels (e.g., at lower temperatures), as compared with certain prior art approaches.

In the illustrated embodiment described above, the cell-disrupting agent 108 comprises heat that is generated by a resistive coil. Any other suitable cell-disrupting agent 108 may also be used in the disruption and/or destruction of tumor cells. For example, in various embodiments, the cell-disrupting agent 108 can comprise any suitable energy form that may be radiated or otherwise delivered to the tumor 54. For example, the cell-disrupting agent 108 can comprise one or more of thermal energy (e.g., resulting from heating elements, radiofrequency ablation devices, and/or ultrasonic devices), electrical energy (e.g., an electric field), and electromagnetic energy (e.g., microwaves). Another example of a cell-disrupting agent 108 is "cold," or the removal of thermal energy (e.g., heat removal). Accordingly, the transfer element 104 can be configured to perform one or more of microwave therapy, radiofrequency ablation, cryotherapy, and irreversible electroporation on the tumor 54. Examples of systems that use certain of such cell-disrupting agents 108 are discussed further below.

Figure 4:
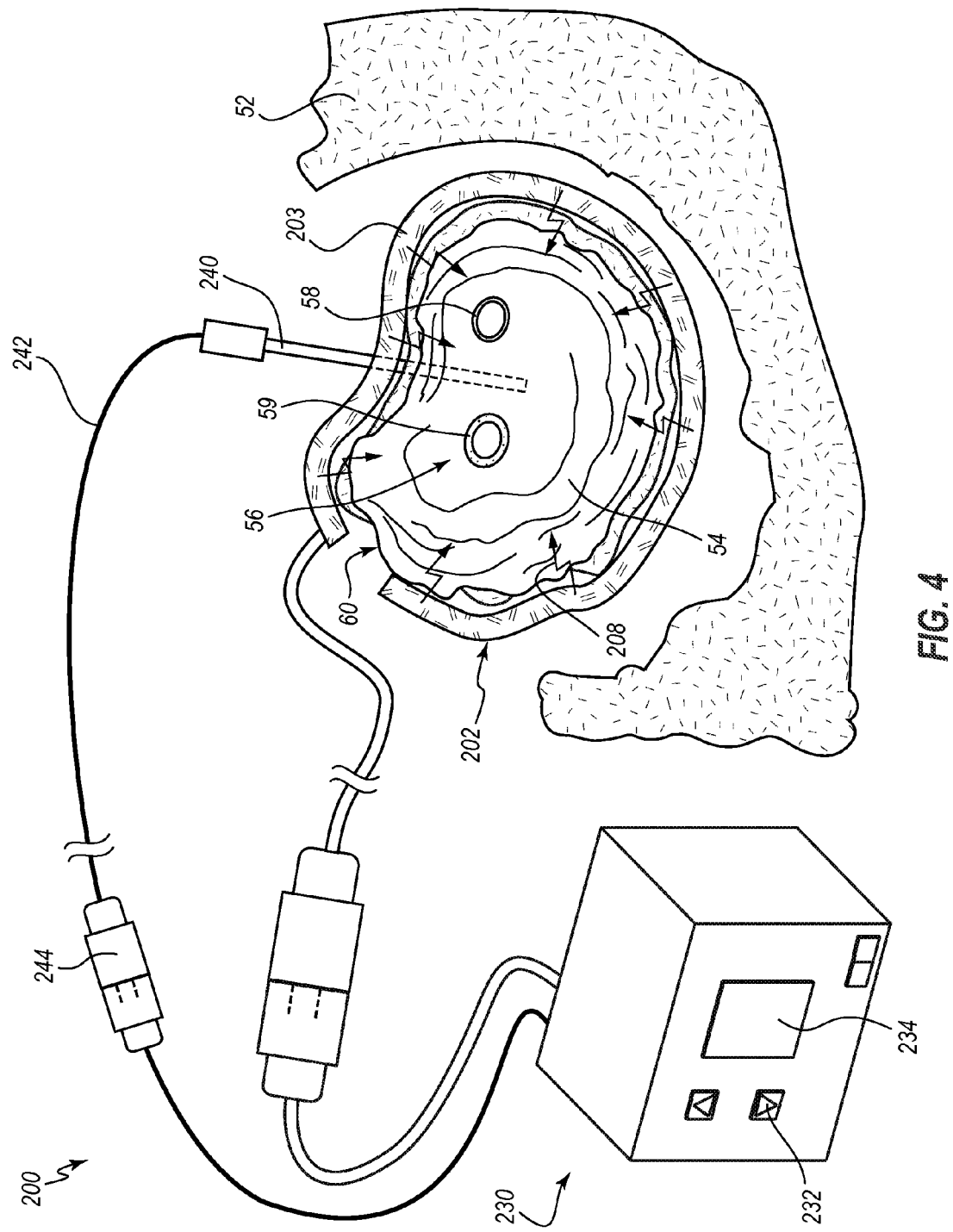
FIG. 4 is a perspective and elevation view of another embodiment of a system for killing tumor cells.

FIG. 4 illustrates another embodiment of a tumor treatment system 200 that can resemble the tumor treatment 100 described above in certain respects. Accordingly, like features are designated with like reference numerals, with the leading digits incremented to "2." Relevant disclosure set forth above regarding similarly identified features thus may not be repeated hereafter. Moreover, specific features of the tumor treatment system 200 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the tumor treatment system 200. Any suitable combination of the features and variations of the same described with respect to the tumor treatment system 100 can be employed with the tumor treatment system 200, and vice versa. This pattern of disclosure applies equally to further embodiments depicted in subsequent figures and described hereafter.

The system 200 can be configured for abating a tumor 54 that has been separated from healthy tissue 52 in a manner such as described above. The system 100 can include a cover 202 that comprises a wrap 203 that is configured to be positioned about at least a portion of the outer border 60 of the tumor 54 and to deliver heat to the tumor 54.

The system 200 can further include a probe 240 that is configured to sense or obtain readings of the presence and/or an amount of a cell-disrupting agent 208. In other or further embodiments, the probe 240 can be configured to sense or obtain readings of the presence and/or an amount of an effect produced by the cell-disrupting agent 208. For example, the probe 240 can comprise any suitable sensor. In the illustrated embodiment, the probe 240 is configured to obtain readings of a temperature of the tumor 54. Accordingly, it may be said that the probe 240 obtains readings of the effect (i.e., raised temperature) produced by the delivery of the cell-disrupting agent 208 (i.e., heat) to the tumor 54. In other embodiments, as discussed below, the cell disrupting agent 208 may instead be electromagnetic energy (e.g., microwaves) that cause heating. In certain of such instances, the probe 240 may obtain readings of the effect (i.e., the raised temperature) produced by the delivery of the cell-disrupting agent 208 (i.e., the electromagnetic energy) to the tumor 54.

The probe 240 can be coupled to a controller 230 in any suitable manner. In the illustrated embodiment, the probe 240 is wired, such that a communication line 252 extends from the probe 240 and is coupled to the controller 230 via a connector 244. In other embodiments, the probe 240 may be wireless. The controller 230 can be configured in any suitable manner so as to obtain, monitor, and/or process readings obtained from the probe 240. The controller 230 may also be configured to control the cover 202 based on information received from the probe 240.

The controller 230 can comprise any suitable data entry devices or hardware, such as dedicated buttons 232, peripheral devices (e.g., keyboard, mouse) or a touchscreen. The controller 230 can also include a display 234 that may indicate the selected settings and/or provide viewable information regarding any suitable parameter of a procedure (e.g., the temperature of the tumor 54 at the position of the probe 240). The controller 230 may include software or dedicated hardware that may be used to implement procedures, such as described hereafter.

In certain procedures, the tumor 54 is separated from the healthy tissue 52 and the cover 202 is applied thereto in manners such as described above. The cell-disrupting agent 208 is then delivered to the tumor 54. For example, the controller 230 can cause current to flow through a resistive heating coil of the cover 202, resulting in heating of the tumor 54. The probe 240 can obtain readings regarding the temperature of the tumor 54.

The temperature readings from the probe 240 may be used by the controller 230 as feedback information, from which the controller 230 may maintain, modulate, adjust, or otherwise control the current that is delivered to the cover 202, and thereby control an amount of heating of the tumor 54. The controller 230 may thus alter an amount of cell-disrupting agent that is delivered from the transfer element 204 in response to one or more readings obtained by the probe 240. In some embodiments, the controller 230 may be configured to terminate heating of the tumor 54 once a predetermined or preprogrammed temperature has been reached, or once that temperature has been maintained for a predetermined or preprogrammed period of time.

In the illustrated embodiment, the probe 240 is positioned to obtain readings at a region that is between the large vessels 58, 59. In some embodiments, blood flow through the vessels 58, 59 can dissipate heat that has been provided by the cover 202. Accordingly, the vessels 58, 59 may tend to shield the inner region of the illustrated tumor 54 from being heated. As a result, the particular placement of the probe 240 may be selected to determine when the coolest portion of the tumor 54 has reached a temperature sufficient to kill cells of the tumor. In some embodiments, multiple probes 240 may be used to monitor different regions of the tumor 54 and then controllably apply heat to the different regions of the tumor 54 to reach temperatures that cause cell disruption. In some instances, it may be desirable to slow or suspend blood flow through the vessels 58, 59 during at least a portion of the period over which the tumor 54 is being treated so as to reduce the heat-sinking effects of the vessels 58, 59. For example, one or more of the vessels 58 may be pinched or occluded at a position that is upstream of the tumor 54 during at least a portion of a procedure.

Accordingly, in various embodiments, methods that utilize the system 200 can include the creation of a margin about at least a portion of the tumor 54. One or more cell-disrupting agents can be applied at an outer surface of the margin and directed inward. An amount of cell-disrupting agent, or an amount of an effect produced thereby, at an interior position of the tumor that is spaced from the margin can be monitored via the probe 240. An amount of the cell-disrupting agent that is delivered to the tumor 54 can be controlled (e.g., maintained, increased, or reduced) based on information received from the probe 240.

Figure 5:
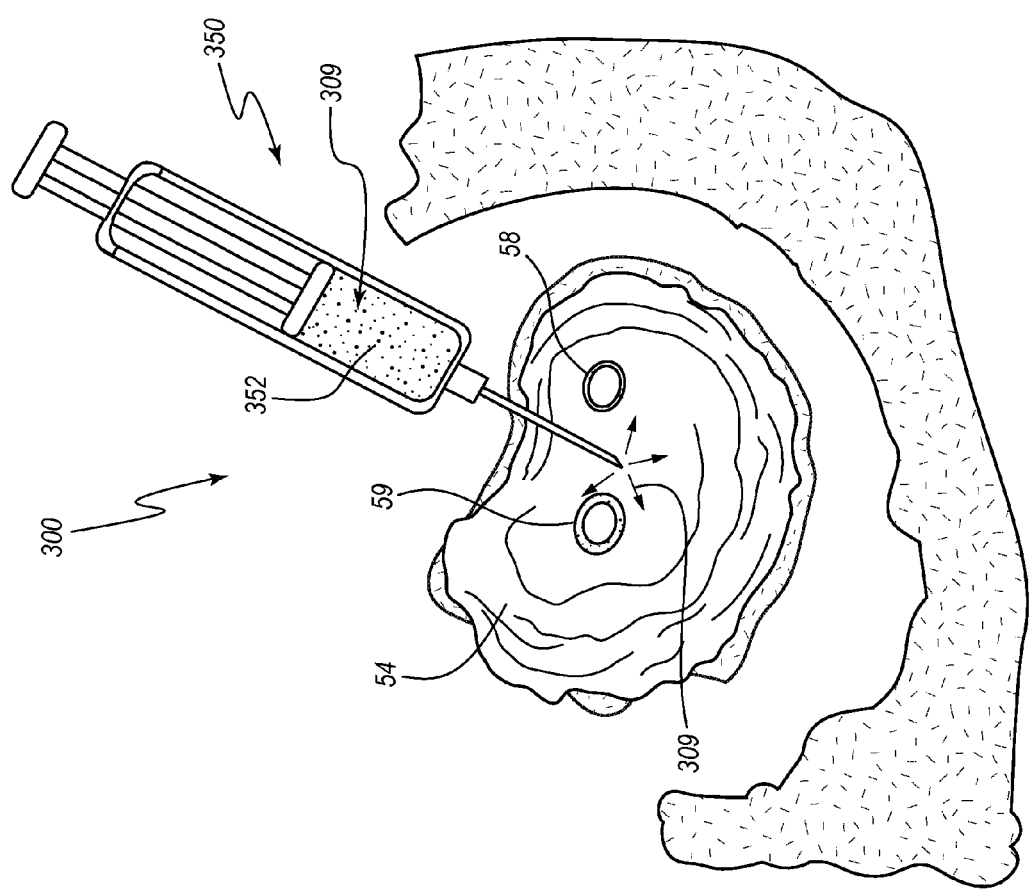
FIG. 5 is an elevation view of a portion of another embodiment of a system for killing tumor cells.
Figure 6:
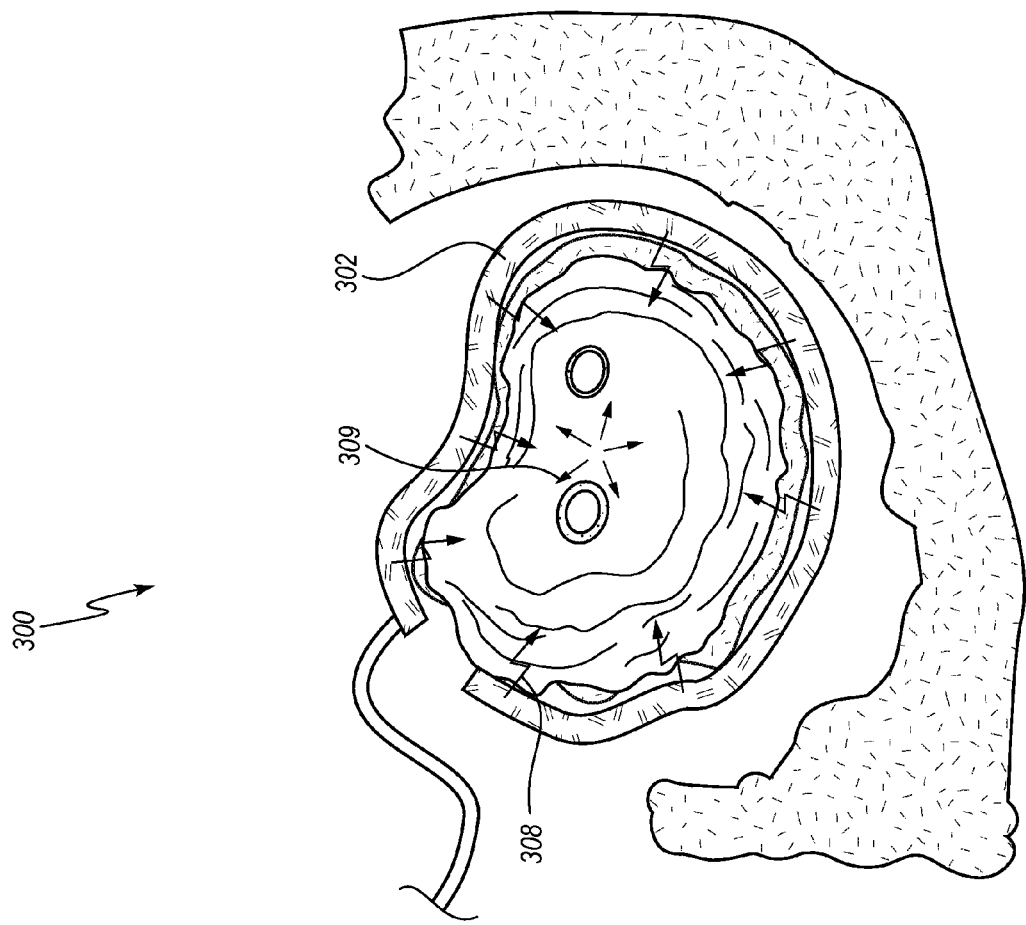
FIG. 6 is an elevation view of another portion of the system of FIG. 5.

FIGS. 5 and 6 illustrate another embodiment of a system 300 that is configured for abating a tumor 54 that has been separated from healthy tissue 52 in a manner such as described above. As previously discussed, in some instances, a tumor 54 may include vessels 58, 59 that dissipate heat, which can thus inhibit heating of those portions of the tumor 54 that are shielded by the vessels 58, 59 to a level sufficient to kill tumor cells. Accordingly, the system 300 can employ a two-pronged approach for abating the tumor by applying a separate cell-disrupting agent to the shielded region.

In FIG. 5, a fluid delivery device 350, such as a syringe, is inserted into the tumor 54 so as to deliver a cell-disruptive agent 309 to the interior of the tumor 54. In the illustrated embodiment, the cell-disruptive agent 309 comprises a chemical ablation fluid 352, such as ethanol, absolute alcohol, or acetic acid. As depicted by the inner arrows in FIGS. 5 and 6, the cell-disruptive agent 309 can move in an outward direction from the distribution site at the tip of the fluid delivery device 350.

As shown in FIG. 6, in some embodiments the system 300 further includes a cover 302 that can operate in any of the manners discussed above. The cover 302 can deliver a cell-disrupting agent 308 to the tumor in the inward direction, as shown by the inwardly directed arrows. The system 300 thus may be particularly well suited for treating tumors that have regions that are at least partially shielded from heating.

FIG. 7 illustrates another embodiment of a system 400 that can be used to abate a tumor. The system 400 can include a cover 402 that is configured to deliver a cell-disrupting agent to a tumor. The cover 402 can resemble the covers described above. In particular, the cover 402 comprises a wrap 403 portion that is configured to be placed in contact with the tumor over at least a portion of an outer periphery thereof.

The wrap 403 can include a transfer element 404 that is configured to deliver a cell-disrupting agent to the tumor. The transfer element 404 comprises a fluid passageway 460 through which fluid can flow. The fluid passageway 460 can comprise a conduit of any suitable variety, such as tubing or the like, or may merely be a void in the material 414 from which the wrap 403 is formed, as shown in FIG. 7A. A generally serpentine pattern for the fluid passageway 460 is depicted in FIG. 7, but any suitable pattern or arrangement is contemplated. An input port 462 can be connected to the fluid passageway 460 at a first end thereof and an output port 464 can be connected to the fluid passageway 460 at an output end thereof.

In operation, a controller or other device can cause fluid (not shown) to flow through the fluid passageway 460 from the input port 462 to the output port 464 when the wrap 403 is in contact with the tumor. In some embodiments, the fluid is heated, such that the cell-disrupting agent delivered by the cover 402 is heat. In other embodiments, the fluid is at a very low temperature, such that the cell-disrupting agent delivered by the cover 402 is heat removal. In still further embodiments, hot and cold fluid may alternatively be passed through the fluid passageway 460 so as to cycle the tumor 54 through alternating heating and cooling periods.

Figure 8:
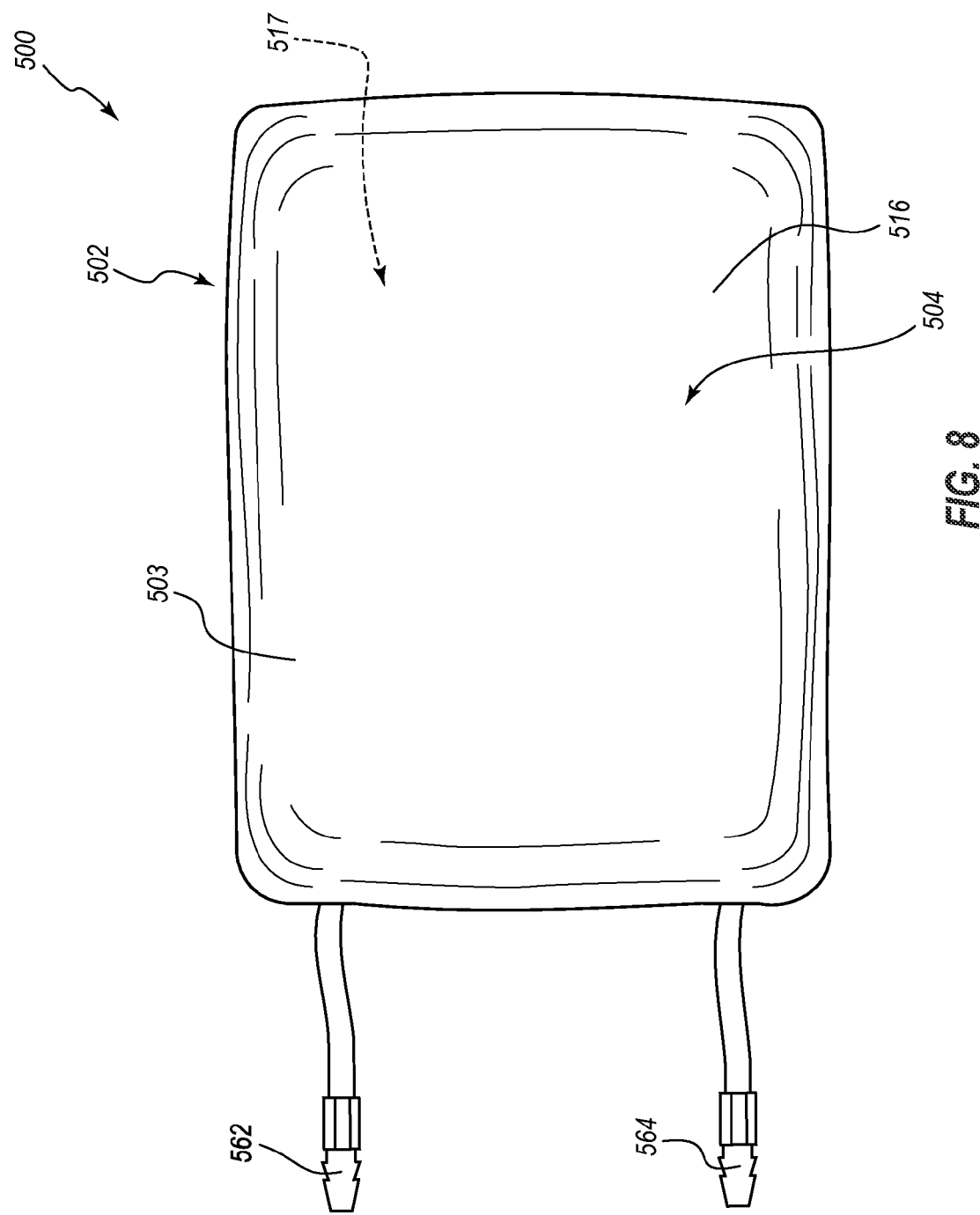
FIG. 8 is a top view of another embodiment of a cover that is compatible with systems for killing tumor cells.

FIG. 8 illustrates another embodiment of a system 500 that can be used to abate a tumor. The system 500 can include a cover 502 that is configured to deliver a cell-disrupting agent to a tumor. The cover 502 comprises a wrap 503 portion that is configured to be placed in contact with the tumor over at least a portion of an outer periphery thereof. The wrap portion 503 can comprise a sleeve 516 of a thermally conducting material that may be relatively flexible and deformable, such as, for example, silicone. A transfer element 504 of the system 500 thus may comprise the sleeve 516, as heat can be transferred across the sleeve 516. The sleeve 516 can define a cavity 517 into which fluid can be received and through which fluid can flow. An input port 562 and an output port 564 can provide ingress and egress to and from the cavity 517.

In operation, a controller or other device can cause fluid to flow through the cavity 517 from the input port 562 to the output port 564 when the wrap 503 is in contact with the tumor 54. In some embodiments, the fluid is heated, such that the cell-disrupting agent delivered by the cover 502 is heat. In other embodiments, the fluid is at a very low temperature, such that heat removal is delivered by the cover 502 as the cell-disrupting agent, or stated otherwise, such that the cover 502 extracts heat from the tumor 54.

Figure 9:
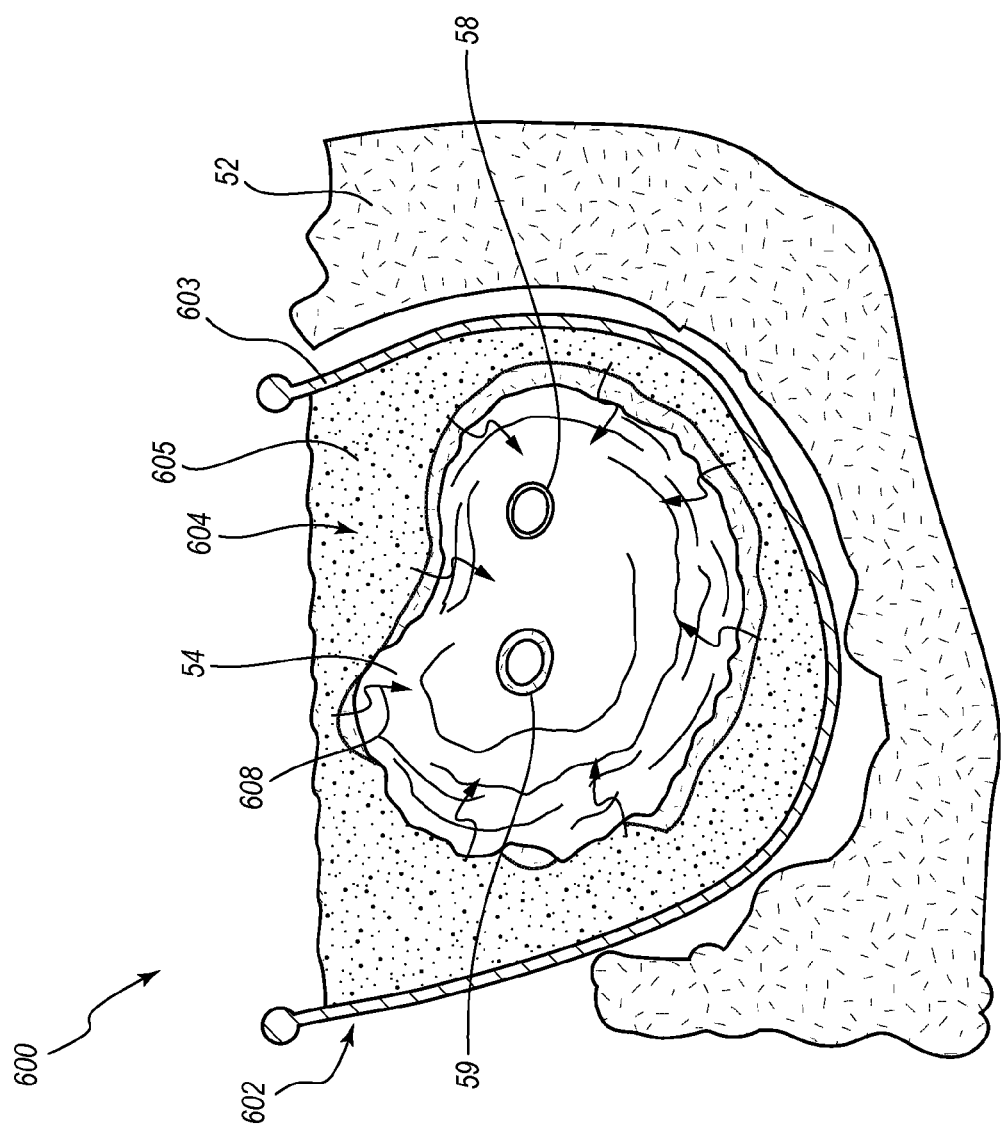
FIG. 9 is a cross-sectional view of another embodiment of a system for killing tumor cells.

FIG. 9 illustrates another embodiment of a system 600 that can be used to abate a tumor. The system 600 can include a cover 602 that is configured for use in the delivery of a cell-disrupting agent to a tumor. The cover 602 comprises a wrap 603 portion that is configured to encompass, envelope, or surround at least a portion of the tumor 54. In the illustrated embodiment, the wrap 603 is spaced from the tumor 54 and extends about a majority of the periphery of the tumor 54, but does not fully encircle the tumor 54. The wrap 603 is shown in partial cross-section in FIG. 9, such that a portion thereof that encompasses the vessels 58, 59 is not shown. However, the portion of the wrap 603 that is not shown can provide a fluid-tight seal about the vessels 58, 59 so as to maintain a transfer element 604 within a reservoir region defined by the wrap 603. In the illustrated embodiment, the transfer element 604 comprises a cell-disrupting fluid 605. The cover 602 thus may also be referred to as a reservoir of cell-disrupting fluid.

In some embodiments, the cell-disrupting fluid 605 comprises a heated or low-temperature fluid such that a cell-disrupting agent 608 that is delivered into the tumor 54 is heat or cold, respectively. In other or further embodiments, the cell-disrupting fluid 605 may comprise a chemical ablation fluid, such as ethanol or acetic acid.

Figure 10:
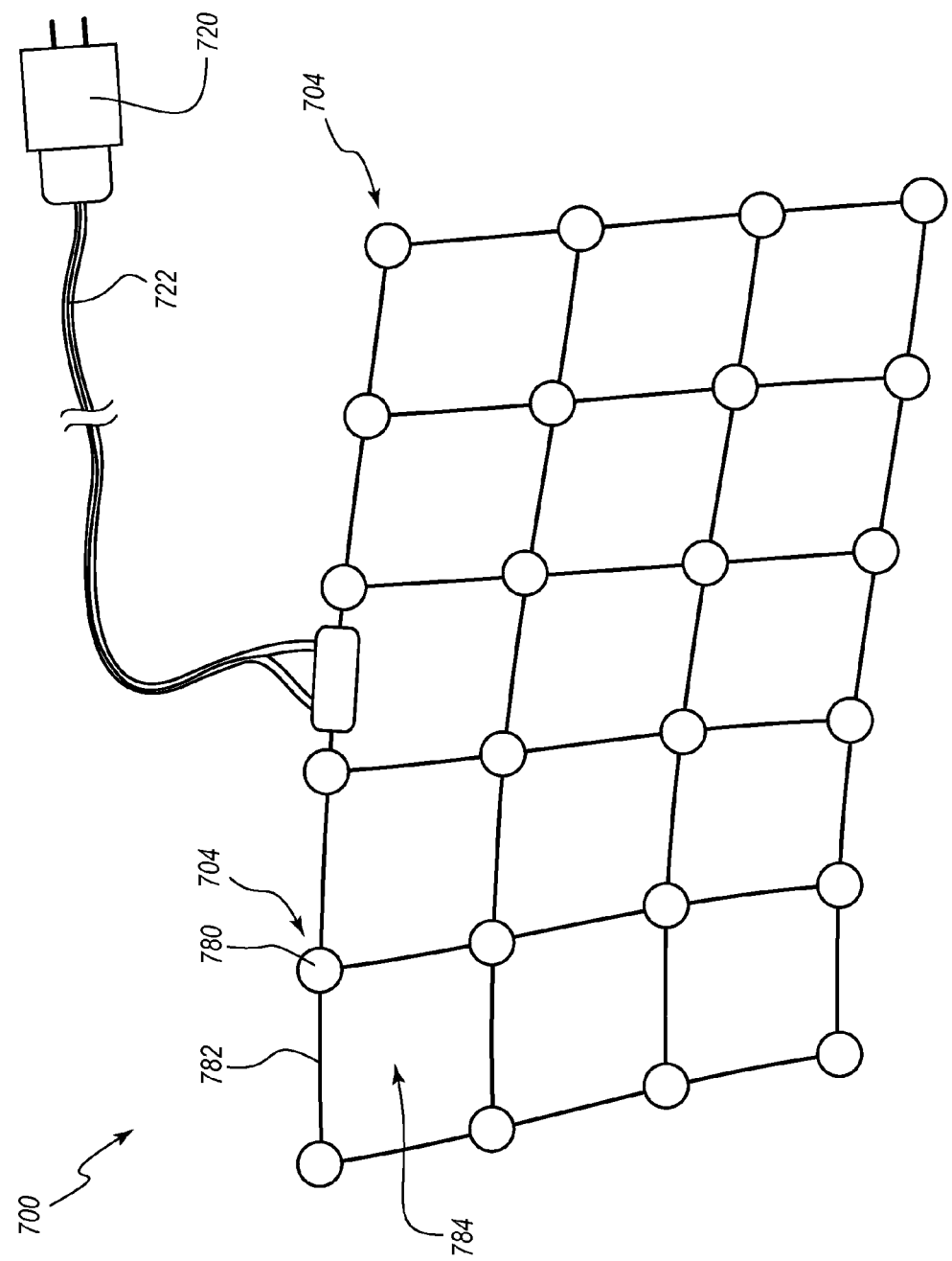
FIG. 10 is a perspective view of another embodiment of a cover that is compatible with systems for killing tumor cells.
Figure 11:
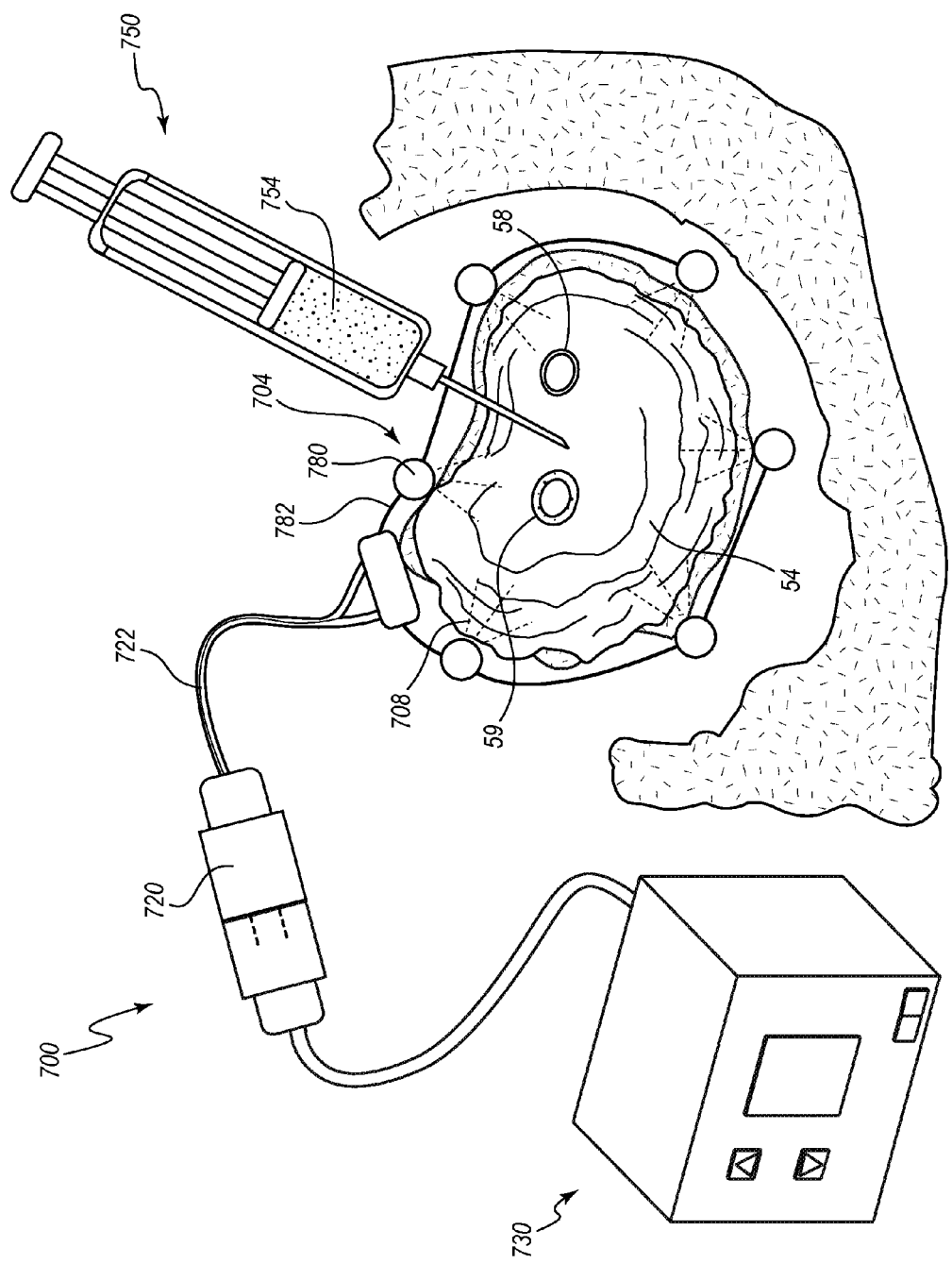
FIG. 11 is a perspective and elevation view of a system for killing tumor cells that utilizes the cover of FIG. 10.

FIGS. 10 and 11 illustrate another embodiment of a system 700 that can be used to abate a tumor. The system 700 can include a cover 702 that is configured for use in the delivery of a cell-disrupting agent to a tumor. In particular, the cover 702 comprises a matrix of light emitters 780 (e.g., light emitting diodes, laser diodes) that are interconnected by electrical leads 782. The cover 702 can further include a lead 722 and connector 720 for coupling the cover 702 with a controller 730. The cover 702 is not a continuous or solid cover, as openings 784 are present between adjacent leads 782 and emitters 780 when the cover 702 is in an expanded orientation, such as shown in FIG. 10.

The cover 702 can be configured to activate an activation fluid 754, which may be delivered to the tumor 54 via a fluid delivery device 750. The activation fluid 754 is configured to be activated to a cell-disruptive state by the cell-disrupting agent 708 that is provided to the tumor from the cover 702. For example, in the illustrated embodiment, the activation fluid 754 comprises a photosensitizer, such as protoporphyrin IX or porfimer sodium (e.g., any suitable Photofrin® product, which is available from Axan Pharma). The activation fluid 754 thus can also be referred to as a cell-disrupting agent. Each of the activation fluid 754 and the light 708 that activates the activation fluid thus may be considered as cell-disrupting agents. The emitters 780 can introduce light into the tumor 54, which can activate the photosensitizer. For example, in some embodiments, the emitters 780 emit light of a particular wavelength that is particularly suited to activation of the photosensitizer. In some embodiments, this activation causes tumor cells to generate free radicals that are toxic to these cells. Other photodynamic therapies are also contemplated. For example, in some embodiments, light may be delivered to the tumor from a source that is spaced from the tumor 54, rather than from a close-fitting cover 702 such as shown in FIG. 11.

In still other embodiments, the activation fluid 754 may comprise a thermosensitizer. For example, the activation fluid 754 may comprise a thermo-responsive porphyrin. The emitters 780 may instead emit microwaves or other electromagnetic radiation that heats the tumor 54 and activates the activation fluid 754. In other embodiments, the cover 102 may be used in conjunction with the thermosensitizer.

In still other embodiments, the activation fluid 754 can comprise conductive ink. The emitters 780 may be replaced with conductive leads that can pass current through the ink so as to heat the tumor 54.

Figure 12:
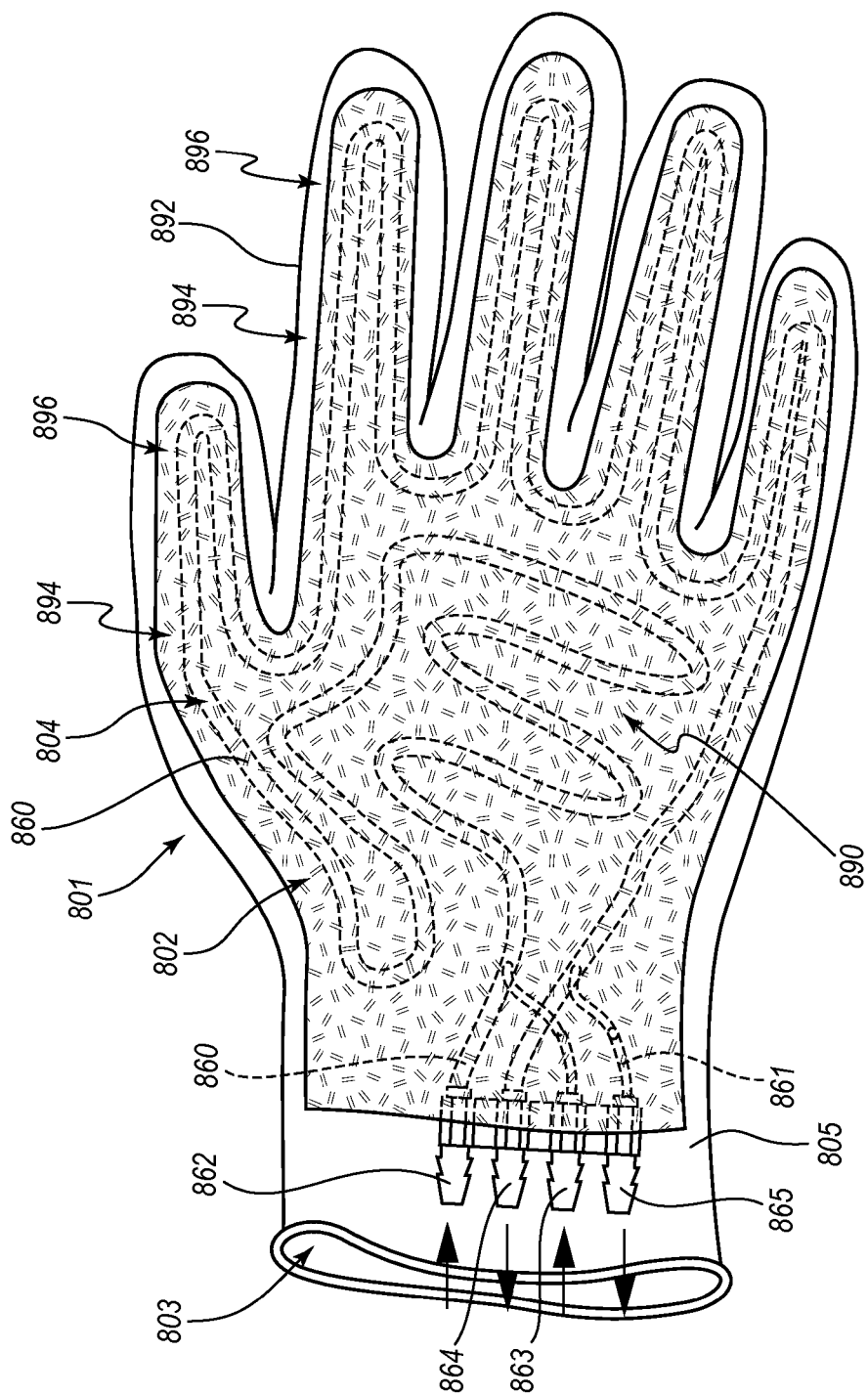
FIG. 12 is an elevation view of another embodiment of a system for killing tumor cells that includes a glove.
Figure 13:
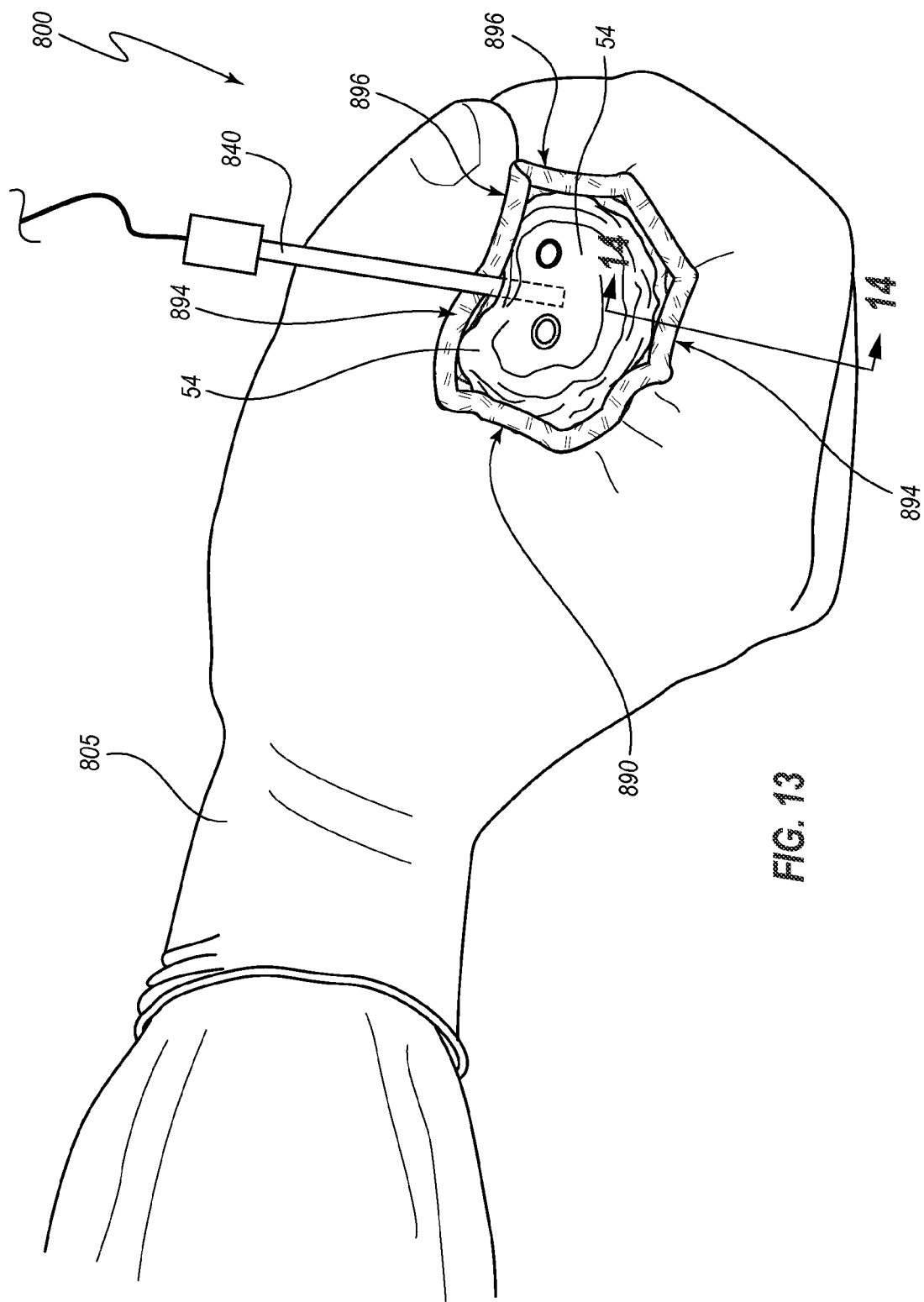
FIG. 13 is an elevation view of the system of FIG. 12 in use.
Figure 14:
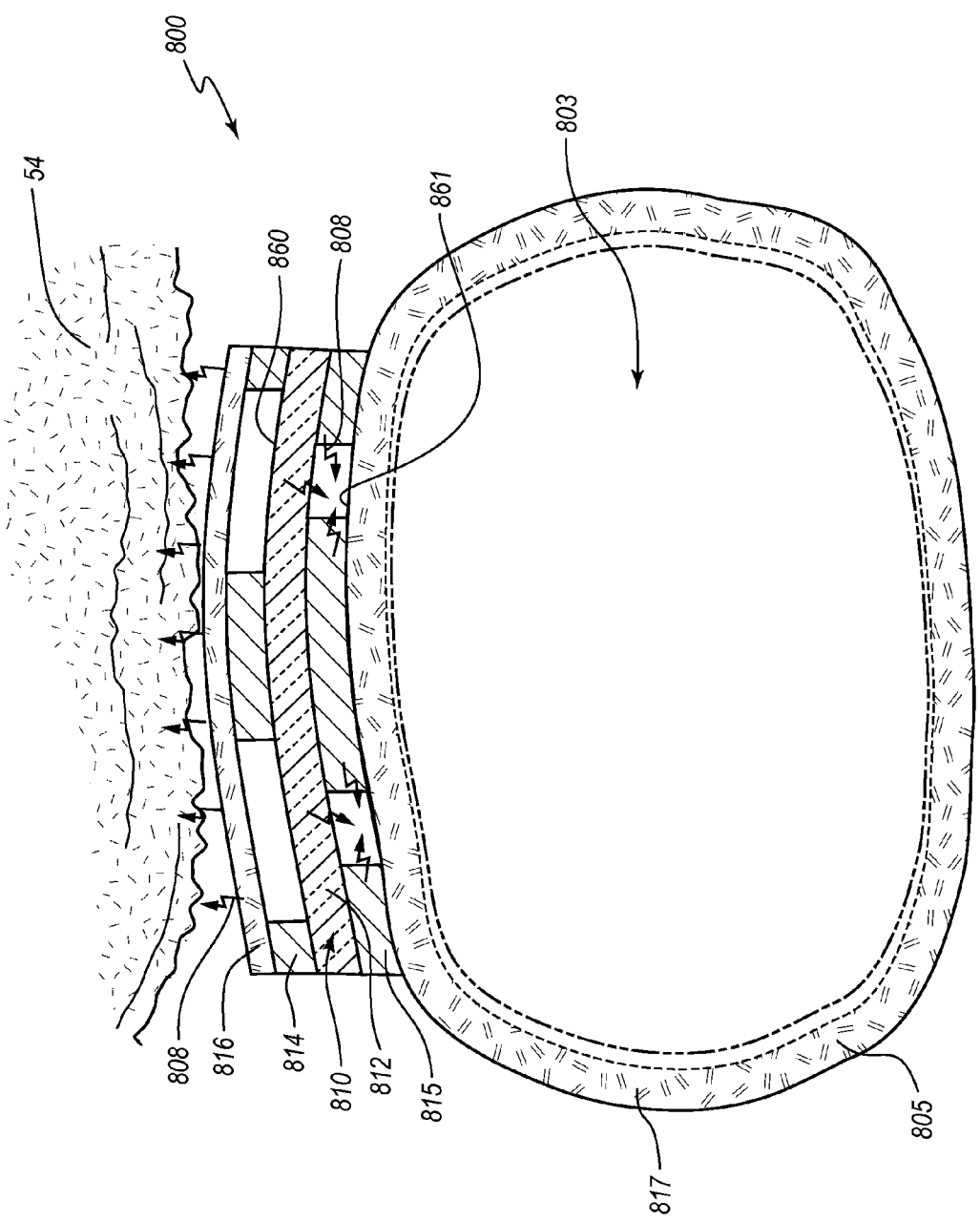
FIG. 14 is a cross-sectional view of the system of FIG. 12 taken along the view line 14-14 in FIG. 13.

FIGS. 12-14 illustrate another embodiment of a system 800 that can be used to abate a tumor. The system 800 comprises a glove 801 that can be worn by a practitioner such that the practitioner can hold the tumor 54 while treating the tumor. In particular, the glove 801 may define a cavity 803 that is sized and shaped to receive the hand of a practitioner therein. Any suitable treatment devices and techniques may be used with the glove 801, such as those discussed above. Similarly, any of the treatment devices and techniques disclosed hereafter with respect to various gloves may be used in systems such as those discussed above.

In the illustrated embodiment, the glove 801 includes base portion 805 that is configured to substantially encompass a hand that has been received into the glove 801. The base portion 805 can comprise any suitable glove arrangement and can comprise any suitable material. For example, the base portion 805 can be similar to standard medical gloves and may comprise latex, silicone, or other suitable materials. The glove 801 can also include a cover 802 that is configured for use in the delivery of a cell-disrupting agent to a tumor. The cover 802 extends over a substantial portion of a front face of the glove 801 such that the cover 802 is directed inwardly when a hand within the glove 801 is clenched (e.g., forms a fist).

The cover 802 can include any suitable cover arrangement described above, although such arrangements may be altered to conform the palm and finger shapes of the glove 801. In particular, the glove 801 can include a palm region 890 and one or more finger sleeves 892 that extend away from the palm region 890. Each finger sleeve 892 can include a trunk region 894 that is adjacent to the palm region 890 and a fingertip region 896 that extends from the trunk region 894 and is spaced from the palm region 890. The cover 802 can extend over at least a portion of the palm region 890 and at least a portion of each of the trunk regions 894 and fingertip regions 896. In the illustrated embodiment 802, the cover 802 is substantially continuous and extends over substantially all of the palm region 890 and over substantially all of each of the trunk regions 894 and fingertip regions 896. The portion of the glove 801 that is configured to contact the tumor 54 during use may also be referred to as a gripping region. In the illustrated embodiment, the gripping region includes the palm region 890, the trunk regions 894, and the fingertip regions 896.

The cover 802 can include a transfer element 804 that is configured to deliver a cell-disrupting agent to the tumor 54. In the illustrated embodiment, the transfer element 804 comprises a fluid passageway 860 through which fluid can flow. The fluid passageway 860 can comprise a conduit of any suitable variety, such as tubing or the like, or may merely be a void or channel within one or more layers that form the glove 801. An input port 862 can be connected to the fluid passageway 860 at a first end thereof and an output port 864 can be connected to the fluid passageway 860 at an output end thereof. The fluid passageway 860 can function in a manner such as described above with respect to the fluid passageway 460.

In the illustrated embodiment, the cover 802 further includes one or more shielding features that are configured to protect a hand that is within the glove 801 from cell-disrupting agents that are delivered to the tumor 54 from the transfer element 804 during use of the glove 801. For example, in the illustrated embodiment, the cover 802 comprises a shielding fluid passageway 861 through which fluid can flow. The shielding fluid passageway 861 can comprise a conduit of any suitable variety, such as tubing or the like, or may merely be a void or channel within one or more layers that form the glove 801. An input port 863 can be connected to the fluid passageway 860 at a first end thereof and an output port 865 can be connected to the fluid passageway 860 at an output end thereof.

As illustrated in FIG. 14, when the glove 801 is in use, a heated fluid can be passed through the transfer element 804 (specifically, the fluid passageway 860) such that a cell-disrupting agent 808 is delivered to the tumor 54. However, the cell-disrupting agent 808 may propagate in directions other than just inwardly toward the tumor 54. In particular, the cell-disrupting agent 808 can propagate outwardly toward the cavity 803 of the glove 801, in which the hand of a practitioner is located. In the absence of shielding features, the cell-disrupting agent 808 could disrupt the cells of the hand. Accordingly, a cooled fluid can be passed through the shielding fluid passageway 861 to thereby dissipate the cell-disrupting agent 808 and prevent it from reaching the hand. In other embodiments, a cooled fluid is passed through the fluid passageway 860 and a heated fluid is passed through the shielding fluid passageway 861. In still further embodiments, heated and cooled fluids may be oppositely cycled through the fluid passageways 860, 861 so as to provide an alternating series of heating/cooling cell-disruptive agents 808 to the tumor 54.

The cover 802 can include additional shielding features. For example, in the illustrated embodiment, the cover 802 comprises a barrier layer 810 that separates the fluid passageways 860, 861. The barrier layer 810 can comprise any suitable insulating material 812.

With continued reference to FIG. 14, the cover 802 can comprise a gripping layer 816 which is configured to contact the tumor 54 when it is held in the glove 801. The gripping layer 816 may be thermally conductive so as allow a large amount of heat to transfer therethrough. The cover 802 can further include a first spacing layer 814 and a second spacing layer 816 that define sidewalls of the fluid passageways 860, 861, respectively. In other embodiments, the spacing layers 814, 816 may instead prevent lateral movement of separate conduits (e.g., tubing) that define the fluid passageways 860, 861.

With reference to FIG. 13, when in use, the glove 801 can be clenched about the tumor 54 such that the gripping region (e.g., the palm region 890 and the trunk and fingertip regions 894, 896) contacts the tumor 54 about a periphery of the tumor 54. In some embodiments, due to the relative stiffness of tumors and/or the materials of which the glove 801 is formed, the user of the glove 801 can receive tactile feedback from the tumor 54 through the glove 801 to determine whether good or firm contact has been made between the cover 802 and the tumor 54. For some embodiments, such as those where thermal transfer to or from the tumor 54 is carried out, such information can be useful to the practitioner, and a grip on the tumor 54 can be selectively adjusted to maintain contact that is conducive to heat transfer.

In some embodiments, the system 800 can include a probe 840, such as the probes discussed above. The probe 840 can be used to measure or monitor a level of a cell-disruptive agent, or effect thereof, within the tumor 54.

With reference again to FIG. 12, in the illustrated embodiment, the glove 801 includes five finger sleeves 892. In other embodiments, the glove 801 may include only a single finger sleeve 892 that is configured to receive multiple fingers therein. For example, the glove 801 may comprise a finger sleeve 892 that is configured to receive a thumb and a transversely expanded finger sleeve 892 that is configured to receive multiple fingers. Accordingly, in some embodiments, the glove 801 may more closely resemble a mitten.

Figure 15:
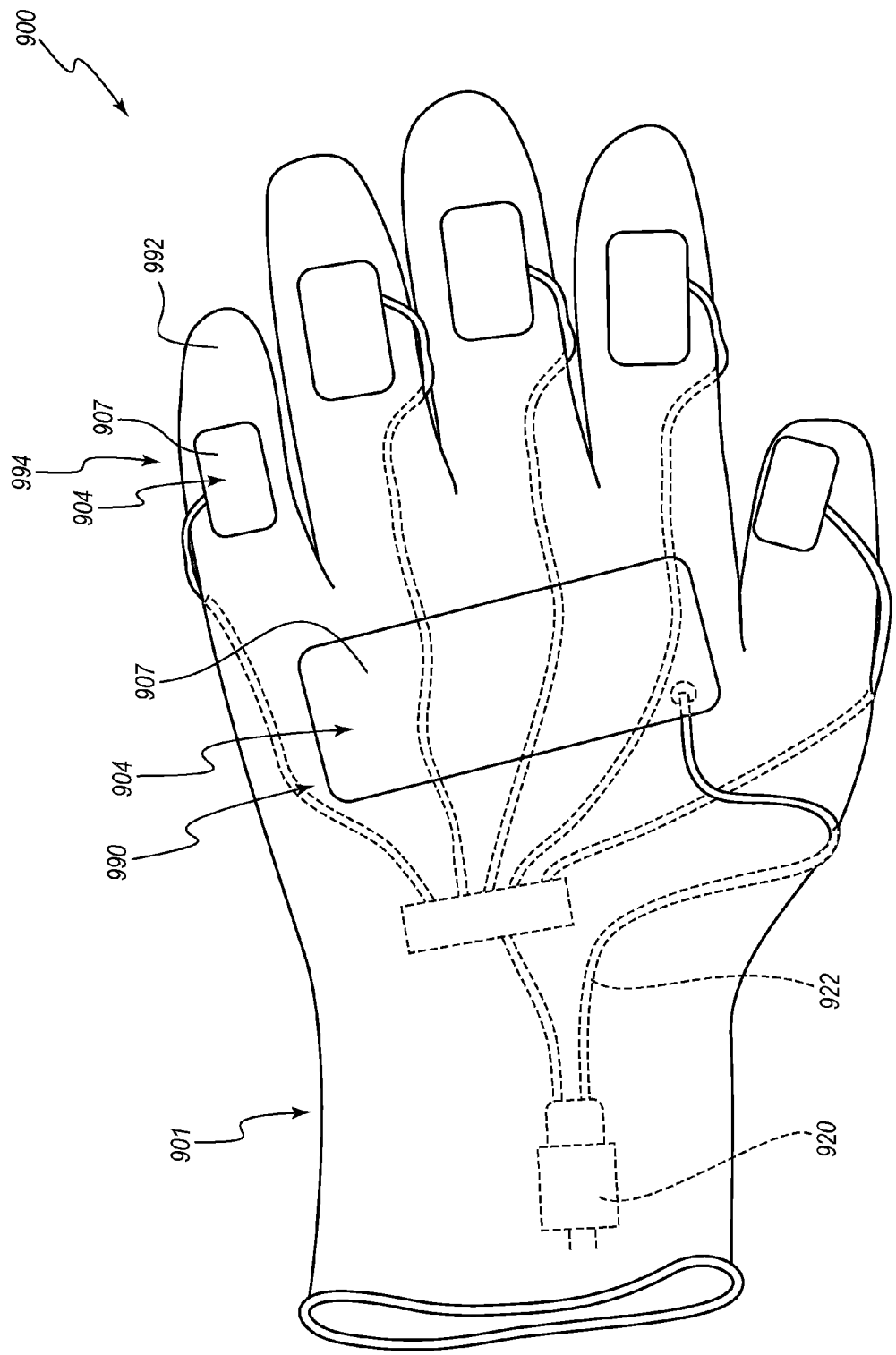
FIG. 15 is an elevation view of another embodiment of a system for killing tumor cells that includes a glove.

FIG. 15 illustrates another embodiment of a system 900 that can be used to abate a tumor. The system 900 comprises a glove 901 such as the glove 801 described above. The glove 901 includes a palm region 990 and multiple finger sleeves 992. The palm region 990 and a trunk region 994 of each finger sleeve 992 comprise transfer elements 904 that are configured to deliver cell-disruptive agents to a tumor 54. In the illustrated embodiment, the transfer elements 904 comprise microwave emitters 907 that are configured to deliver microwaves to the tumor 54. A connector 920 can be configured to interface with a controller. Leads 922 can extend between the connector and the emitters 907.

In other or further embodiments, the features of the gloves 801 and 901 can be combined. For example, a glove can be configured to heat the tumor 54 by both circulating heated fluid through a fluid passageway and by providing microwaves to the tumor 54 via one or more microwave emitters.

Figure 16:
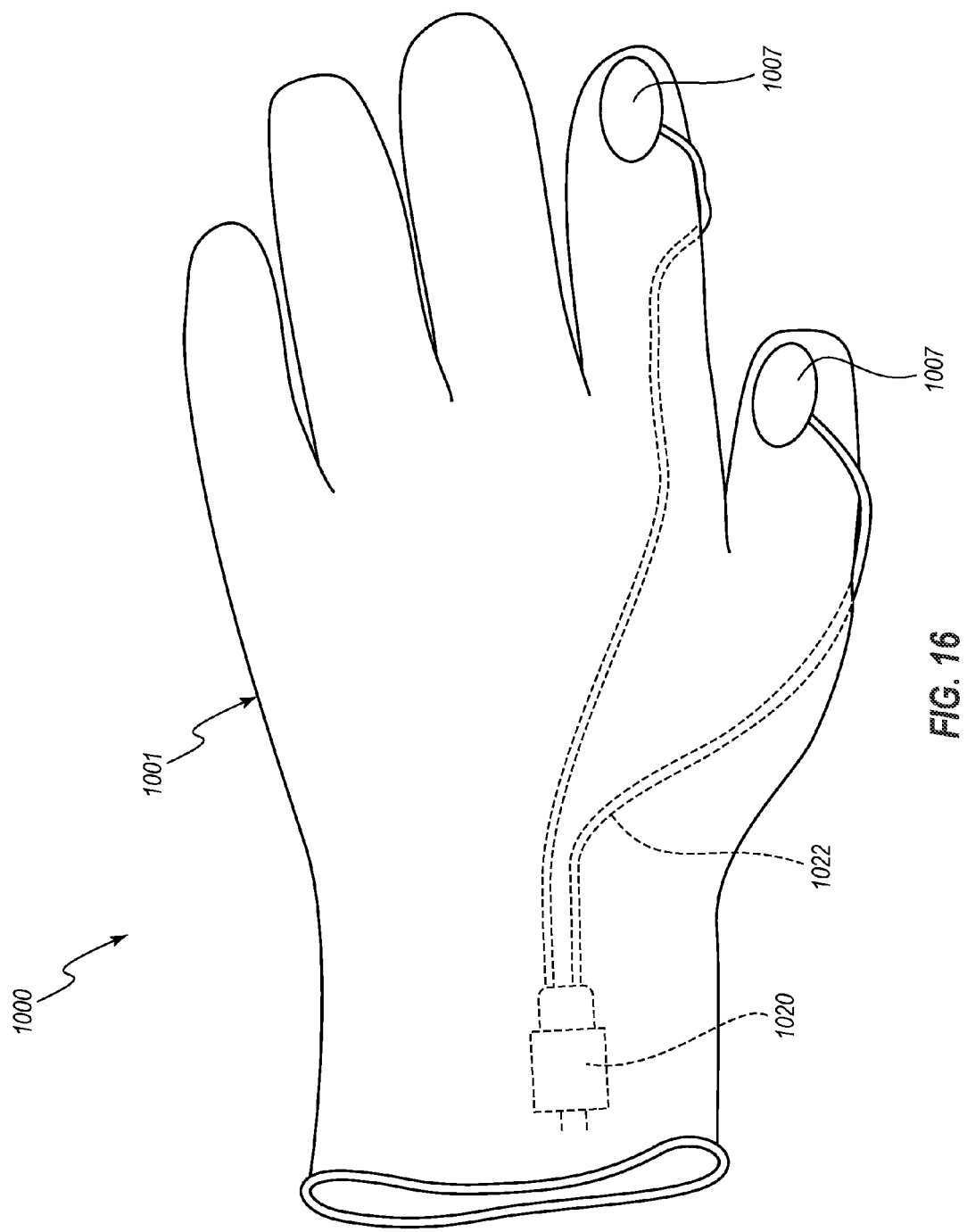
FIG. 16 is an elevation view of another embodiment of a system for killing tumor cells that includes a glove.
Figure 17:
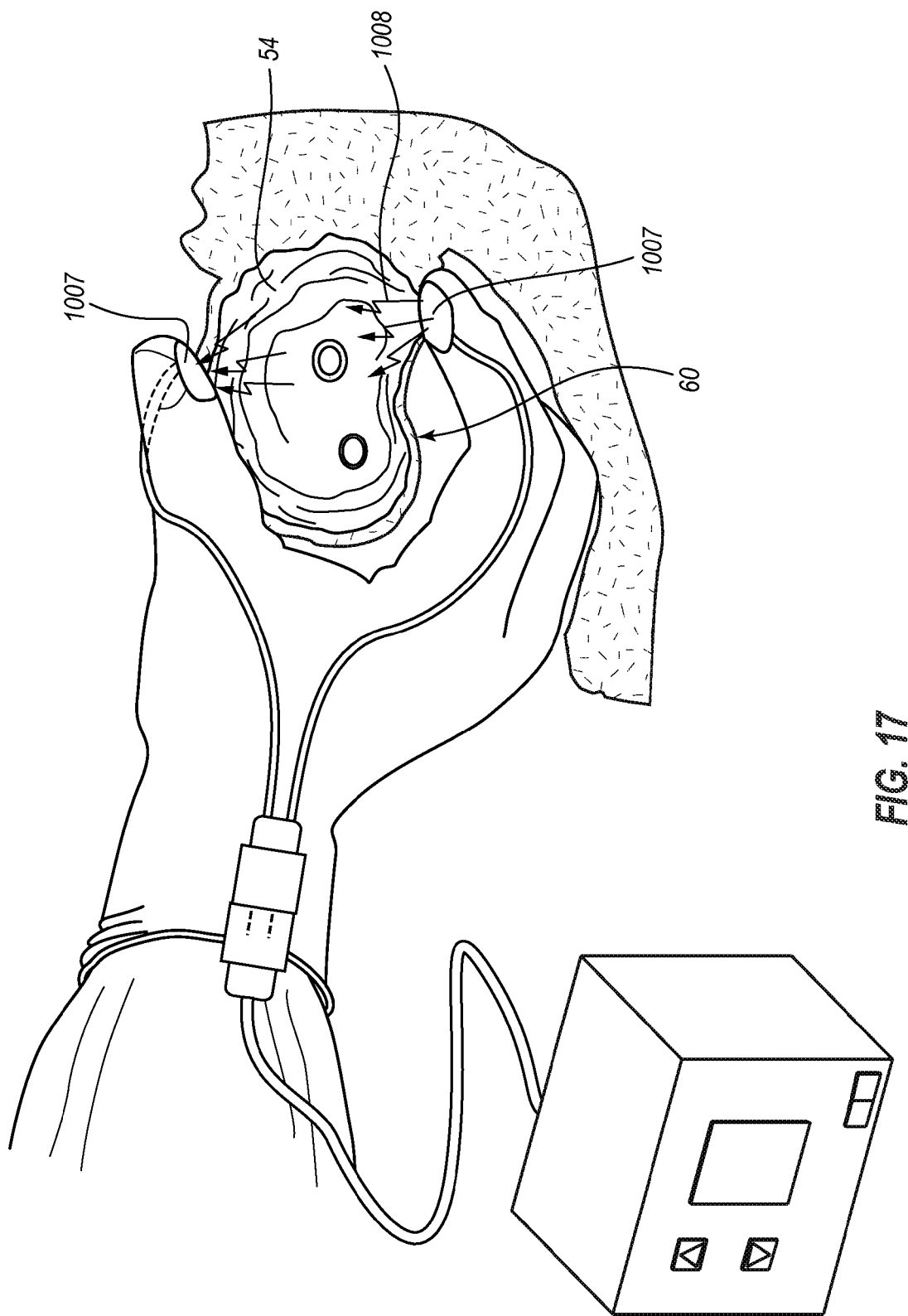
FIG. 17 is an elevation view of the system of FIG. 16 in use.

FIGS. 16 and 17 illustrate another embodiment of a system 1000 that can be used to abate a tumor. The system 1000 comprises a glove 1001 such as the gloves 801, 901 described above. The glove 1001 comprises electrodes 1007 at fingertips thereof. In particular, the glove 1001 comprises a first electrode 1007 at a tip of a thumb sleeve and comprises a second electrode 1007 at a tip of an index finger sleeve. A connector 1020 can be configured to interface with a controller. Leads 1022 can extend between the connector 1020 and the electrodes 1007.

As shown in FIG. 17, the electrodes 1007 can be configured to introduce a cell-disrupting agent 1008 into the tumor 54. In the illustrated embodiment, the cell-disrupting agent 1008 comprises an electrical field of sufficient strength to cause irreversible electroporation of the tumor cells. In some embodiments, the tumor 54 is not fully separated from surrounding healthy tissue prior to use of the glove 1001. Rather, in the illustrated embodiment, diametrically opposing sides of the tumor 54 are exposed so as to permit the electrodes 1007 to be placed at the opposing sides.

FIGS. 18-24 illustrate an embodiment of a glove 1101 that can be used to separate a tumor from surrounding healthy tissue and/or for other suitable purposes. The glove 1101 may be referred to as a surgical glove. Although in the illustrated embodiment of the glove 1101, only the surgical features are shown, in other embodiments, the glove 1101 can include features such as described above with respect to the gloves 801, 901, 1001. For example, in some embodiments, the glove 1101 is configured to be used to clench the tumor 54 and deliver a cell-disrupting agent thereto.

Figure 18:
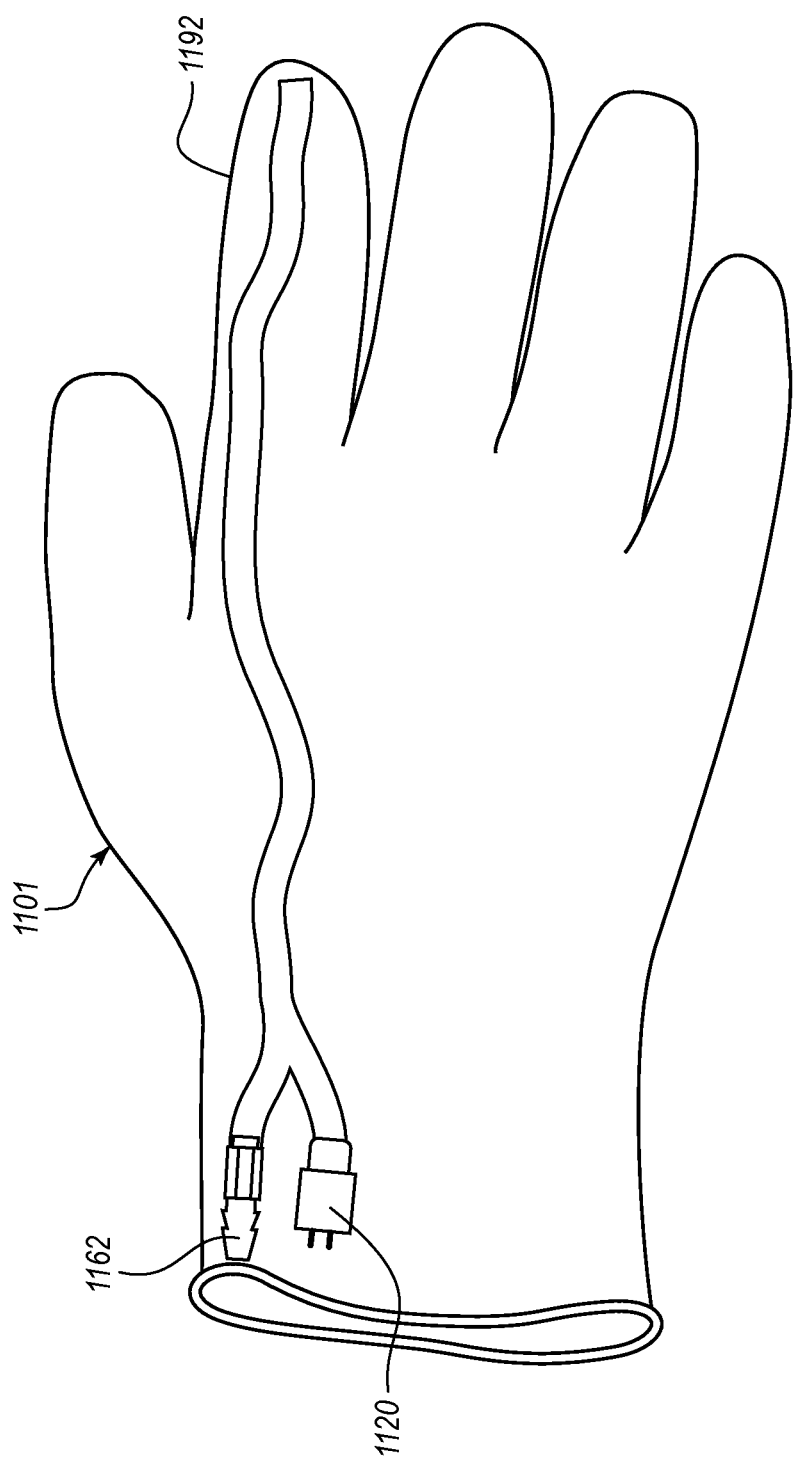
FIG. 18 is an elevation view of an embodiment of a glove that is configured for use in electrosurgical applications.

As shown in FIG. 18, the glove 1101 can include a plurality of finger sleeves 1192. An electrosurgical assembly, as further discussed hereafter, can be positioned along one of the finger sleeves 1192. In the illustrated embodiment, the assembly is positioned along the index finger sleeve, although other finger sleeves are options.

In many instances, tumors are so large that a surgeon may typically perform dissection of areas behind the tumor by feel, rather than by sight and sharp dissection. The glove 1101 can be of particular utility in such situations, as the glove 1101 is configured to deliver energy from a finger tip that can be used to cut and coagulate the tissues that can be felt by the surgeon, but not seen. This can enhance the safety of such dissection procedures and can decrease the risk of bleeding and complications to the patient.

Figure 19:
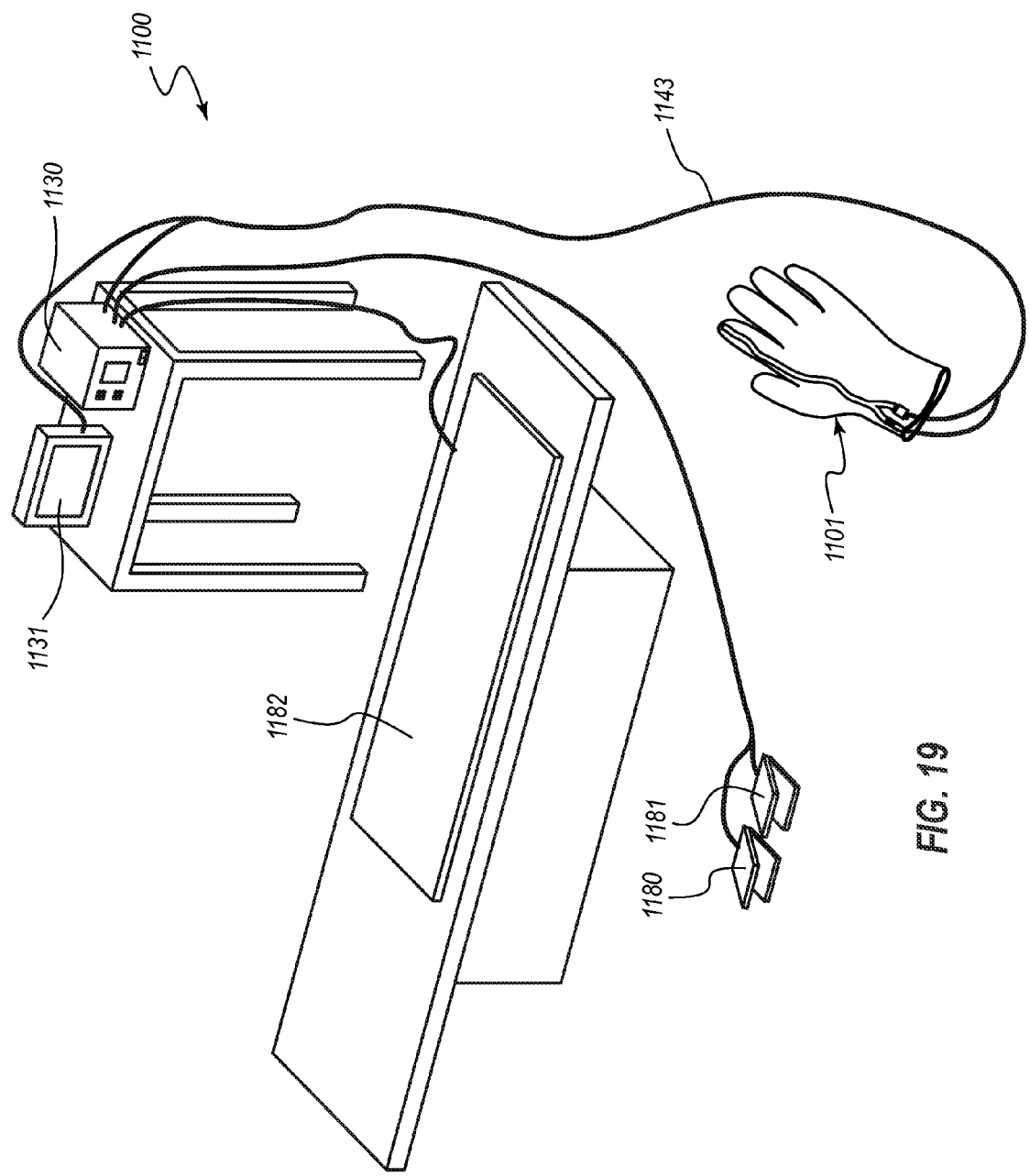
FIG. 19 is a perspective view of an embodiment of a system with which the glove of FIG. 18 is compatible.

FIG. 19 illustrates a system 1100 in which the glove 1101 can be used. The system 1100 includes one or more control lines 1143 that connect the glove 1101 to a controller 1130. In some embodiments, the glove 1101 may have photographic or videographic capabilities such that a monitor 1131 may be provided for viewing of images obtained by the glove 1101. In some embodiments, a surgery table on which a patient is positioned includes a grounding pad 1182. The system 1100 may also include foot pedals 1180, 1181 by which a practitioner can control various features of the system 1100 during surgery.

Figure 21:
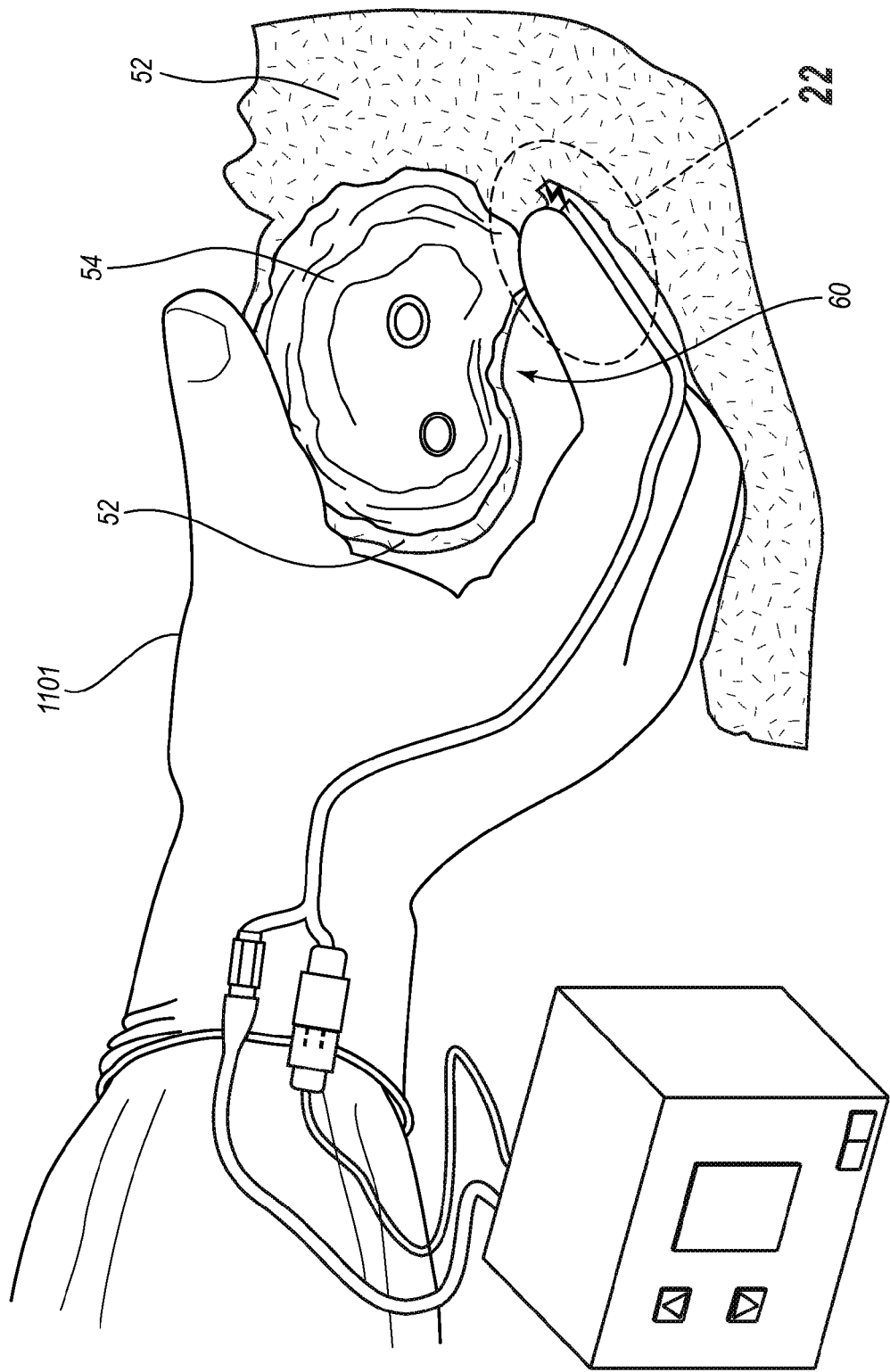
FIG. 21 is a perspective and elevation view of the system of FIG. 19 in use.

FIGS. 20-23 illustrate various views of the glove 1101 in use during a surgical procedure. As shown in FIGS. 20 and 21, the glove 1101 can emit energy from a fingertip thereof so as to separate the tumor 54 from healthy tissue 52 and thereby form a border 60 about a periphery of the tumor 54

Figure 22:
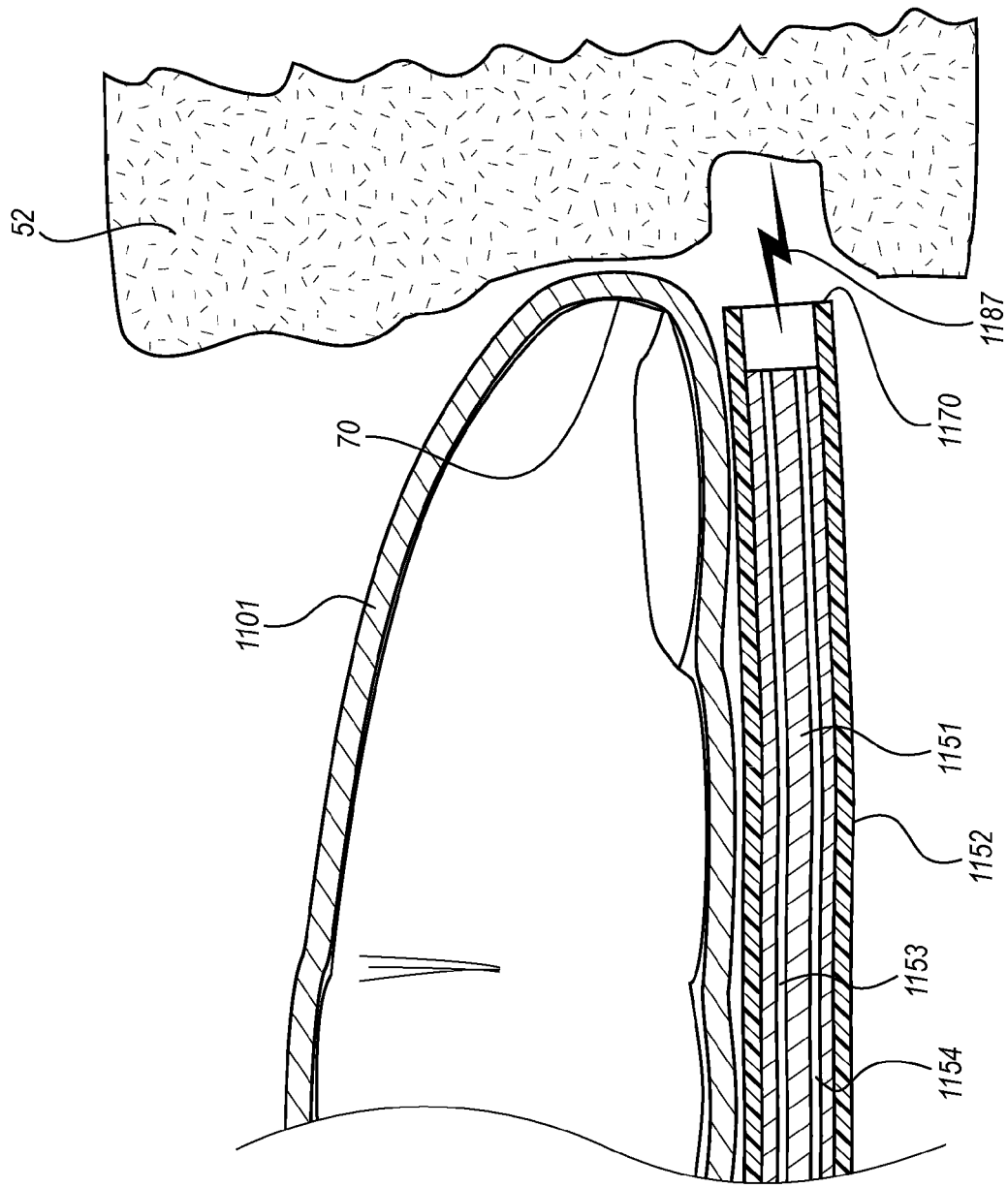
FIG. 22 is a partial side cross-sectional view of the system of FIG. 19 in use.
Figure 23:
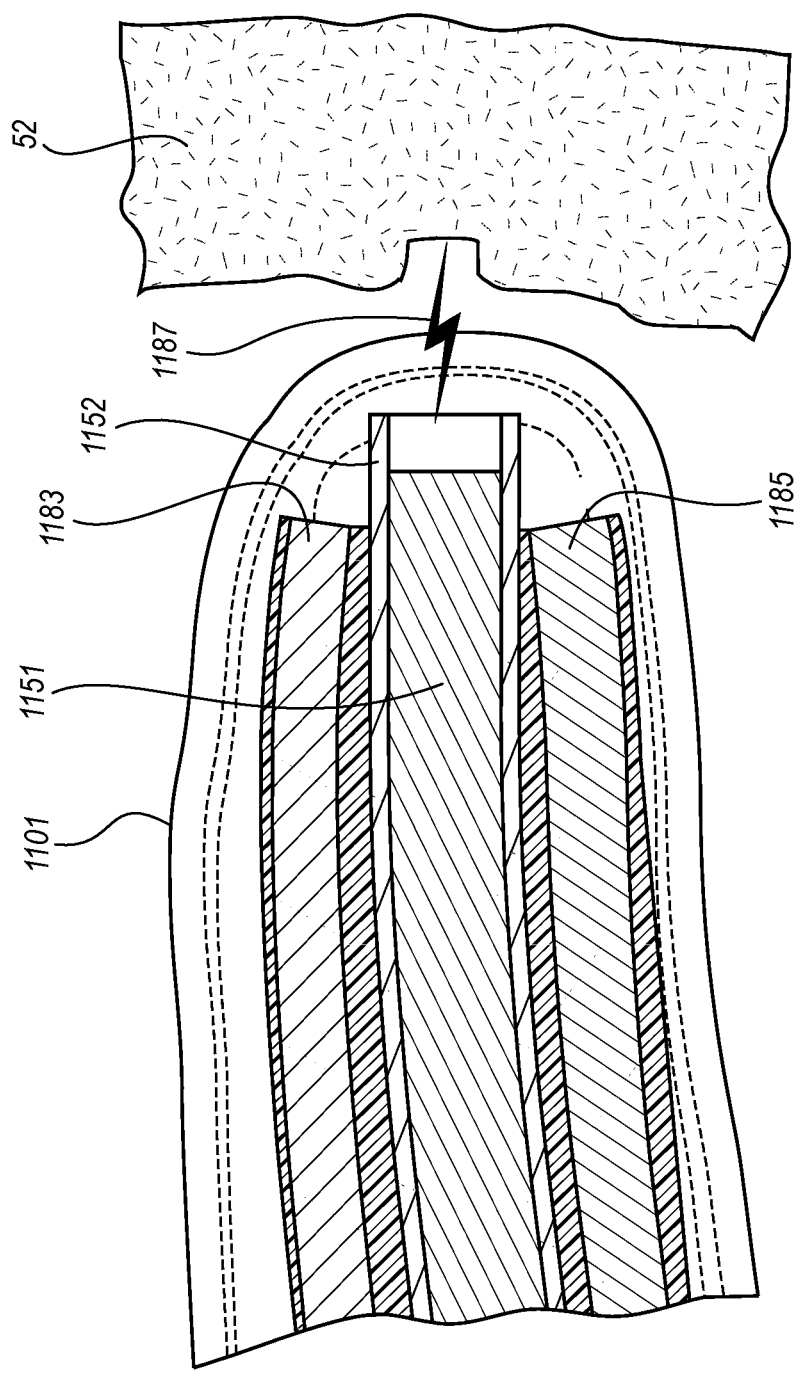
FIG. 23 is a partial top cross-sectional view of the system of FIG. 19 in use.
Figure 24:
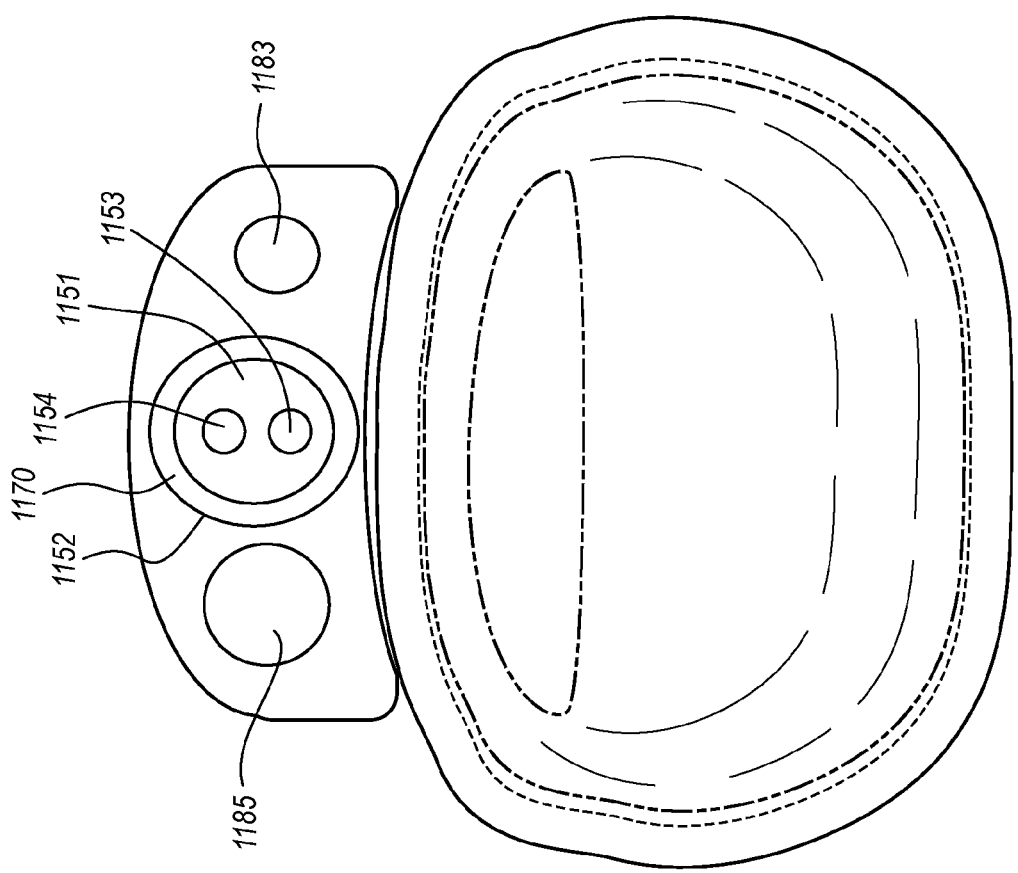
FIG. 24 is a front elevation view of the system of FIG. 19.

FIGS. 22-24 illustrate various features of the electrosurgical assembly of the glove 1101. The glove 1101 includes an electrode 1151 from which electrical energy can be transmitted, as schematically shown by the bolt 1187. In the illustrated embodiment, the electrode 1151 is encased by a layer of insulation 1152. The insulation 1152 extends beyond a distal tip of the electrode 1151 and may serve to focus the electrical energy that is transmitted from the electrode 1151. In the illustrated embodiment, a distal tip 1170 of the insulation 1152, from which the electrical energy is directed in a focused manner, is aligned with a distal tip 70 of a finger that is within the glove 1101. Such an arrangement can provide a natural feel to a surgeon in determining where cutting, ablation, coagulation, or the like is taking place.

In the illustrated embodiment, one or more channels 1153, 1154 are provided through the electrode 1151. The channels may be used to provide a purging fluid (e.g., a gas) to the surgical site. As shown in FIG. 18, the glove 1101 can include a port 1162 through which the purging fluid is provided. The glove 1101 also can include a connector 1120 by which the glove 1101 is coupled to the controller 1130 (FIG. 19) and via which energy is supplied to the glove 1101.

FIGS. 23 and 24 illustrate that the glove 1101 can include a light source 1183 and an imaging device 1185, which can be used to obtain images from the surgical site. The imaging device 1185 can be configured to obtain visible light images of the surgical site. In other embodiments, ultrasound or other suitable imaging devices may be used, which may or may not be used in conjunction with a light source 1183.

Certain features of electrosurgery that may be used in the system 1100 are well known in the art, and thus are not detailed in the foregoing discussion. For example, some electrosurgical features that may be used with the system 1100 are disclosed in U.S. Patent Application Publication No. 2004/0250281, which published on Dec. 23, 2004, and is titled FINGER TIP ELECTROSURGICAL MEDICAL DEVICE.

Figure 25:
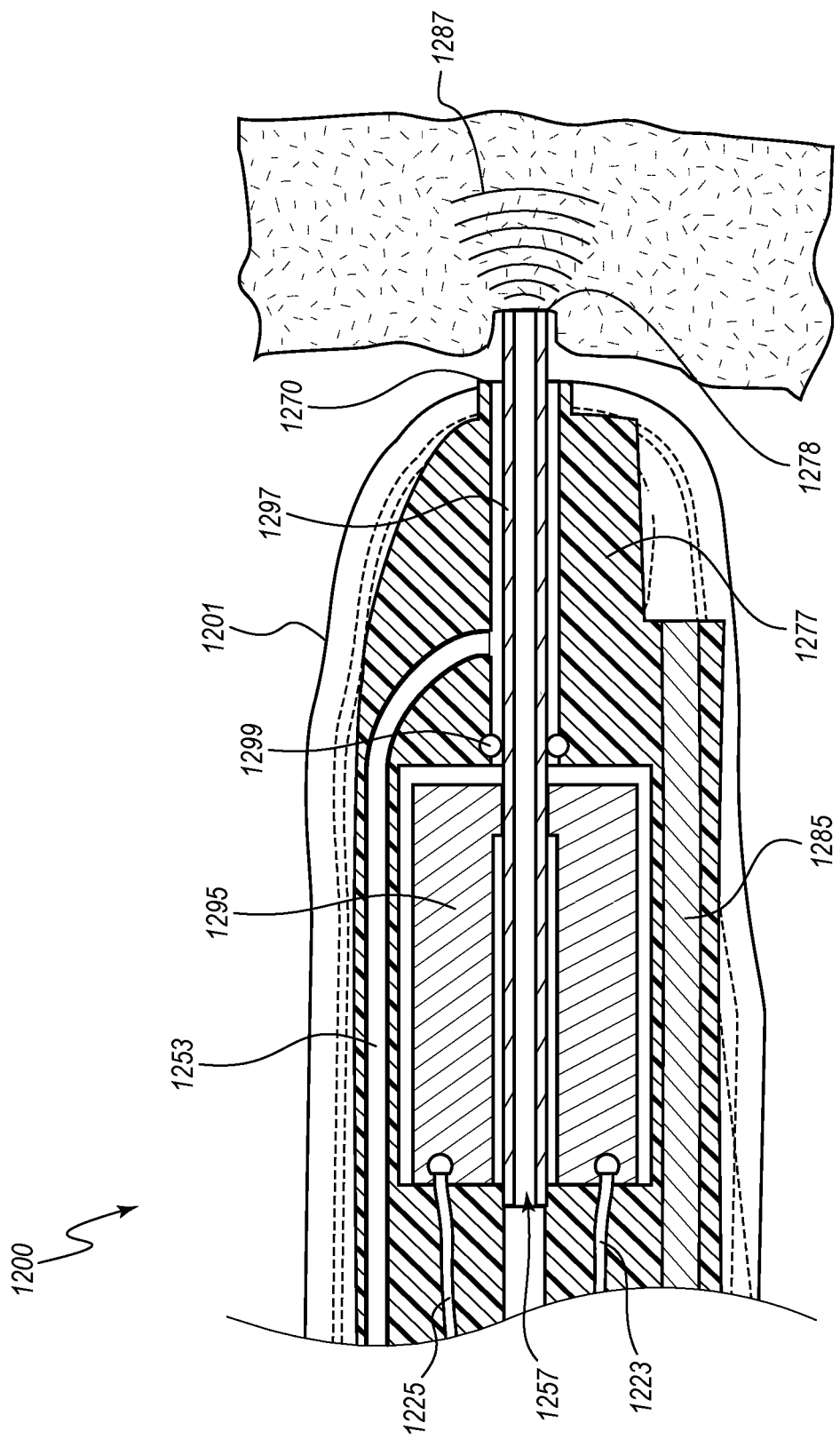
FIG. 25 is a top cross-sectional view of a portion of an embodiment of a glove that is configured for use in ultrasonic surgical applications.

FIG. 25 illustrates an embodiment of a system 1200 that is similar to the system 1100, except that ultrasonic ablation is used for surgical cutting, rather than electrosurgical cutting. A finger assembly portion of a glove 1201 can include a piezoelectric driver 1295 having electrical leads 1223, 1225 connected thereto. The driver 1295 is configured to vibrate a tip 1297 at ultrasonic speeds so as to transmit vibration energy 1287 into the tissue. In some embodiments, the glove 1201 can include a fluid purge line 1253. A seal 1299, such as an O-ring, can prevent fluid that is delivered via the purge line 1253 from coming into contact with the driver 1295. In some embodiments, a suction channel 1257 can extend through the tip 1297 and can be used to clear liquefied material from a distal end 1278 of the vibration tip 1297.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially planar" is recited with respect to a feature, it is understood that in further embodiments, the feature can have a precisely planar orientation.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x],"where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. §112 ¶ 6. Embodiments of the invention in which an exclusive property or privilege is claimed are defined as follows.

The invention claimed is:

1. A method of killing cells of a tumor, the method comprising:

separating the tumor from neighboring tissue so as to define an exposed outer border about at least a portion of the tumor that is spaced from the neighboring tissue;

after said separating, positioning a cover that comprises a transfer element between the neighboring tissue and the outer border, the cover comprising a flexible blanket formed of a continuous piece of material;

wrapping the cover about the tumor;

introducing a probe comprising a sensor into an interior region of the tumor;

introducing a cell-disrupting agent into the tumor via the transfer element; and monitoring an amount of cell-disrupting agent at the interior region of the tumor using readings obtained by the sensor.

2. The method of claim 1, further comprising altering an amount of cell-disrupting agent that is delivered from the transfer element in response to one or more readings obtained by the sensor.

3. The method of claim 1, wherein the cell-disrupting agent comprises at least one of heat, electrical energy, and electromagnetic energy.

4. The method of claim 1, wherein the cell-disrupting agent comprises heat removal.

5. The method of claim 1, wherein the transfer element performs at least one of microwave therapy, radiofrequency ablation, cryotherapy, and irreversible electroporation on the tumor.

6. The method of claim 1, wherein the transfer element comprises one or more of a conduit through which a heated or cooled fluid flows, a resistive heater, a microwave emitter, and an electrode.

7. The method of claim 1, wherein the cover comprises one or more additional transfer elements, wherein each transfer element is directed inwardly so as to deliver a cell-disrupting agent to the tumor, and wherein the cell-disrupting agents delivered from the transfer elements comprise one or more of heat, removal of heat, electrical energy, and electromagnetic energy.

8. The method of claim 1, wherein the transfer element extends about at least a majority of a perimeter of the tumor when the cover has been wrapped about the tumor.

9. The method of claim 1, wherein the cover comprises a barrier and the transfer element is at a first side of the barrier, and wherein the barrier prevents the cell-disrupting agent from entering into the neighboring tissue that is at a second side of the barrier.

10. The method of claim 1, wherein a portion of healthy tissue that is immediately adjacent to the tumor is separated from the neighboring tissue such that the outer border extends about both the tumor and the separated portion of healthy tissue.

11. The method of claim 1, wherein one or more of a blood vessel and a nerve pass through the tumor, wherein separating the tumor from neighboring tissue is performed without severing the blood vessel and/or the nerve, and wherein the cover is positioned about the blood vessel and/or the nerve.

12. The method of claim 11, wherein the probe is introduced into the interior region of the tumor so as to detect a level of cell-disrupting agent at a position near the blood vessel and/or the nerve, and wherein the sensor is a temperature sensor.

13. The method of claim 1, wherein said wrapping the cover about the tumor comprises conforming the cover to a contour defined by the outer border.

14. The method of claim 13, wherein said wrapping the cover about the tumor comprises positioning the cover to extend along at least a majority of a perimeter of the contour.

15. The method of claim 14, wherein the cover extends continuously along said at least a majority of the perimeter of the contour.

16. The method of claim 13, wherein said wrapping the cover about the tumor comprises positioning the cover to extend along a full perimeter of the contour.

17. The method of claim 1, wherein said wrapping the cover about the tumor comprises positioning the cover to encompass the tumor about at least a majority of a perimeter of the tumor.

18. The method of claim 1, wherein said separating the tumor from neighboring tissue so as to define the exposed outer border yields an open gap between the neighboring tissue and the outer border.

19. A method of killing cells of a tumor, the method comprising:

separating the tumor from neighboring tissue so as to define an exposed outer border about at least a portion of the tumor;

after said separating, positioning a cover that comprises a transfer element between the neighboring tissue and the outer border, the cover comprising a flexible blanket;

wrapping the cover about the tumor;

introducing a probe comprising a sensor into an interior region of the tumor;

introducing a cell-disrupting agent into the tumor via the transfer element; and monitoring an amount of cell-disrupting agent at the interior region of the tumor using readings obtained by the sensor.

20. The method of claim 19, wherein said wrapping the cover about the tumor comprises conforming the cover to a contour defined by the outer border.

21. The method of claim 19, wherein the flexible blanket can be shaped to form a substantially planar surface when not wrapped around the tumor.

22. A method of killing cells of a tumor, the method comprising:

separating the tumor from neighboring tissue so as to define an exposed outer border about at least a portion of the tumor;

after said separating, positioning a cover that comprises a transfer element between the neighboring tissue and the outer border, the cover comprising a flexible blanket;

conforming the cover to a contour defined by the outer border;

securing the cover to the tumor;

introducing a probe comprising a sensor into an interior region of the tumor;

introducing a cell-disrupting agent into the tumor via the transfer element; and monitoring an amount of cell-disrupting agent at the interior region of the tumor using readings obtained by the sensor.

\* \* \* \* \*